(12) United States Patent
Heeney et al.

(10) Patent No.: US 7,674,397 B2
(45) Date of Patent: Mar. 9, 2010

(54) REACTIVE MESOGENIC CHARGE TRANSPORT COMPOUNDS

(75) Inventors: Martin Heeney, Southampton (GB); Weimin Zhang, Southampton (GB); Steven Tierney, Southampton (GB); David Sparrowe, Bournemouth (GB); Maxim Shkunov, Southampton (GB); Iain McCulloch, Southampton (GB)

(73) Assignee: Merck Patent Gesellschaff mit beschrankter Haftung, Darmstadt (DE)

( * ) Notice: Subject to any disclaimer, the term of this patent is extended or adjusted under 35 U.S.C. 154(b) by 1155 days.

(21) Appl. No.: 11/066,007

(22) Filed: Feb. 25, 2005

(65) Prior Publication Data

US 2005/0184274 A1     Aug. 25, 2005

Related U.S. Application Data

(60) Provisional application No. 60/547,068, filed on Feb. 25, 2004.

(30) Foreign Application Priority Data

Mar. 11, 2004   (EP) .................................. 04005797

(51) Int. Cl.
    C09K 19/34    (2006.01)
    C09K 19/38    (2006.01)
    C07D 333/04   (2006.01)
    C07D 333/46   (2006.01)
    C07D 409/04   (2006.01)
    C07D 409/14   (2006.01)
    H01B 1/12     (2006.01)

(52) U.S. Cl. .............. 252/299.61; 252/299.3; 252/299.5; 252/500; 549/59; 549/62; 549/66; 528/380

(58) Field of Classification Search ............ 252/299.01, 252/299.5, 299.3, 299.61, 500; 549/59, 62, 549/66; 528/380
See application file for complete search history.

(56) References Cited

FOREIGN PATENT DOCUMENTS

| EP | 1275650 A2 | 6/2002 |
|----|------------|--------|
| EP | 1275652 A2 | 1/2003 |
| EP | 1279689 A2 | 1/2003 |
| EP | 1279690 A1 | 1/2003 |
| EP | 1279691 A1 | 1/2003 |
| EP | 1284258 A2 | 2/2003 |
| EP | 1300480 A1 | 4/2003 |
| EP | 1318185 A1 | 6/2003 |
| EP | 1357163 A1 | 10/2003 |
| EP | 1398336 A1 | 3/2004 |
| WO | WO 03/006468 A2 | 1/2003 |

OTHER PUBLICATIONS

Allard et al., "Oligothiophenes for Pattern Formation by Stamping", Macromol. Chem. Phys. 2003, 204, 68-75.*
Allard et al., "Micro- and nanostructuring of oligo- and polythiophenes in two and three dimensions", Electrochimica Acta 48 (2003) 3137-3146.*

* cited by examiner

*Primary Examiner*—Shean C Wu
(74) *Attorney, Agent, or Firm*—Millen, White, Zelano & Branigan, P.C.

(57) ABSTRACT

The invention relates to new reactive mesogenic compounds with charge transport properties comprising at least two thiophene groups, their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices, and to a field effect transistor, light emitting device or ID tag comprising the reactive mesogenic charge transport compounds.

25 Claims, No Drawings

REACTIVE MESOGENIC CHARGE TRANSPORT COMPOUNDS

This application claims the benefit of the filing date of U.S. Provisional Application Ser. No. 60/547,068 filed Feb. 25, 2004.

FIELD OF INVENTION

The invention relates to new reactive mesogenic compounds with charge transport properties comprising at least two thiophene groups. The invention further relates to their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices. The invention further relates to a field effect transistor, light emitting device or ID tag comprising the reactive mesogenic charge transport compounds.

BACKGROUND

Organic materials have recently shown promise as the active layer in organic based thin film transistors and organic field effect transistors [see H. E. Katz, Z. Bao and S. L. Gilat, *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semi-conducting material and the current on/off ratio, so the ideal semiconductor should have a low conductivity in the off state, combined with a high charge carrier mobility ($>1\times10^{-3}$ cm$^2$V$^{-1}$ s$^{-1}$). In addition, it is important that the semi-conducting material is relatively stable to oxidation i.e. it has a high ionisation potential, as oxidation leads to reduced device performance.

A known compound which has been shown to be an effective p-type semiconductor for OFETs is pentacene [see S. F. Nelson, Y. Y. Lin, D. J. Gundlach and T. N. Jackson, *Appl. Phys. Lett.*, 1998, 72, 1854]. When deposited as a thin film by vacuum deposition, it is shown to have carrier mobilities in excess of 1 cm$^2$ V$^{-1}$ s$^{-1}$ with very high current on/off ratios greater than $10^6$. However, vacuum deposition is an expensive processing technique that is unsuitable for the fabrication of large-area films.

Regular poly(3-hexylthiophene) has been reported with charge carrier mobility between $1\times10^{-5}$ and $4.5\times10^{-2}$ cm$^2$ V$^{-1}$ s$^{-1}$, but with a rather low current on/off ratio between 10 and $10^3$ [see Z. Bao et al., *Appl. Phys. Lett.* 1997, 78, 2184]. In general, poly(3-alkylthiophenes) show improved solubility and are able to be solution processed to fabricate large area films. However, poly(3-alkylthiophenes) have relatively low ionisation potentials and are susceptible to doping in air [see H. Sirringhaus et al., *Adv. Solid State Phys.* 1999, 39, 101].

It was an aim of the present invention to provide new organic materials for use as semiconductors or charge transport materials, which are easy to synthesise, have high charge mobility and good processability. The materials should be easily processable to form thin and large-area films for use in semiconductor devices. Another aim as to extend the pool of semiconducting materials available to the expert. Other aims of the invention are immediately evident to those skilled in the art from the following description.

It was found that the above aims can be achieved by providing reactive mesogenic compounds according to the present invention. They consist of a central mesogenic core comprising two or more thiophene rings, and optionally one or more phenylene rings that form a conjugated system together with the thiophene rings, said mesogenic core being linked, optionally via a spacer group, to one or more reactive groups. The compounds can induce or enhance liquid crystal phases or are liquid crystalline themselves. They can be oriented in their mesophase and the polymerisable group can be polymerised or crosslinked in situ to form polymer films with a high degree of order, thus yielding improved semiconductor materials with high stability and high charge carrier mobility.

A further aspect of the invention relates to liquid crystal polymers, in particular liquid crystal side chain polymers obtained from the reactive mesogenic compounds according to the present invention, which are then further processed e.g. from solution as thin layers for use in semiconductor devices.

Reactive mesogenic compounds for semiconducting applications have been described in WO 03/006468 A2, EP 1 275 650 A2, EP 1 275 652 A2, EP 1 279 690 A1, EP 1 279 691 A1, EP 1 279 689 A2, EP 1 284 258 A2, EP 1 318 185 A1, EP 1 300 430 A1, EP 1 357 163 A1, EP 1 398 336 A1 and 1. McCulloch et al., *J. Mater. Chem.* 2003, Vol. 13, p. 2436-2444.

DEFINITION OF TERMS

The term 'liquid crystal or mesogenic material' or 'liquid crystal or mesogenic compound' should denote materials or compounds comprising one or more rod-shaped, board-shaped or disk-shaped mesogenic groups, i.e. groups with the ability to induce-liquid crystal phase behaviour. Liquid crystal compounds with rod-shaped or board-shaped groups are also known in the art as 'calamitic' liquid crystals. Liquid crystal compounds with a disk-shaped group are also known in the art as 'discotic' liquid crystals. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'reactive group' or 'reactive compound' means compounds or groups that are capable of participating in a polymerisation reaction, like radicalic or ionic polymerisation from unsaturated functionality, or a polyaddition or polycondensation reaction, as well as compounds or groups that are capable of being grafted for example by a condensation or addition reaction to a reactive polymer backbone in a polymeranaloguous reaction.

The term 'film' includes self-supporting, i.e. free-standing, films that show more or less pronounced mechanical stability and flexibility, as well as coatings or layers on a supporting substrate or between two substrates.

SUMMARY OF THE INVENTION

The invention relates to compounds of formula I

wherein
P is a polymerisable or reactive group,
Sp is a spacer group or a single bond,
X is a linkage group or a single bond, $A^1$ and $A^2$ are independently of each other 1,4-phenylene or thiophene-2,5-diyl, all of which are optionally substituted with one or more groups $R^1$, $R^1$ has one of the meanings of R, $Z^1$ is are independently of each other —O—, —S—, —CO—, —COO—, —OCO—, —O—COO—, —CO—$NR^0$—, —$NR^0$—CO—, —O—CO—$NR^0$—, —$NR^0$—CO—O—, —$NR^0$—CO—$NR^0$—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—COO—, —OCO—CH=CH— or a single bond, $R^0$ and $R^{00}$ are independently of each other H or alkyl with 1 to 12 C-atoms, $Y^1$ and $Y^2$ are independently of each other H, F, Cl or CN, R is H, halogen, CN, $NO_2$, NCS, $SF_5$, $Sn(R')_3$, SiR'R"R'" straight chain, branched or cyclic alkyl with 1 to 30 C-atoms, which is unsubstituted, mono- or polysubstituted by F, Cl, Br, I or CN, and wherein one or more non-adjacent $CH_2$ groups are optionally replaced, in each case independently from one another, by —O—, —S—, —NH—, —$NR^0$—, —SiR'R"—, —CO—, —COO—, —OCO—, —OCO—O—, —S—CO—, —CO—S—, —$CY^1$=$CY^2$— or —C≡C— in such a manner that O and/or S atoms are not linked directly to one another, an aromatic or heteroaromatic group, or P—Sp—X, R', R" and R'" are independently of each other alkyl with 1 to 12 C-atoms, and m is 1, 2, 3, 4 or 5, with the provisos that a) at least two of $A^1$ and $A^2$ are optionally substituted thiophene-2,5-diyl, and b) $A^1$ and $A^2$ are different from

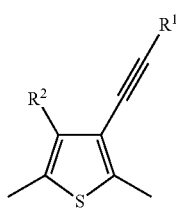

wherein $R^2$ is $R^1$ or —C≡C—$R^1$ and the groups $R^1$ have independently of each other one of the meanings of R given above.

The invention also relates to the use of the compounds of formula I as semiconductors or charge transport materials, in particular in optical, electro-optical or electronic devices, like for example in field effect transistors as components of integrated circuitry, as thin film transistors in flat panel display applications or RFID tags, or in semi-conducting components for organic light emitting diode (OLED) applications such as electroluminescent displays or backlights of flat panel displays, for photovoltaic or sensor devices, or as light-modulating components for liquid crystal displays, optical films or other optical or electrooptical devices.

The invention also relates to a field effect transistor, for example as a component of integrated circuitry, as a thin film transistor in flat panel display applications, or in an RFID tag, comprising one or more compounds according to the present invention.

The invention also relates to a semi-conducting component, for example in OLED applications like electroluminescent displays or backlights of flat panel displays, in photovoltaic or sensor devices, comprising one or more according to the present invention.

DETAILED DESCRIPTION OF THE INVENTION

The reactive mesogenic compounds according to the present invention provide several advantages over prior art materials by adding substituent-chains and other groups to the mesogenic core they can be made more soluble, thus being suitable for spin coating or solution coating techniques, rather than vacuum deposition, to prepare thin films for use e.g. in electronic devices such as transistors, they can be made mesogenic or liquid crystalline, thus exhibiting a higher degree of order that leads to particularly high charge carrier mobility, in particular when being aligned in their mesophase into macroscopically ordered orientation their macroscopic mesophase properties can be frozen in by in situ polymerisation, they combine the properties of a semi-conducting material with those of a mesogenic material to give novel materials with a rigid, planar conjugated core and a flexible chain to increase solubility and to decrease the melting point, which show high charge carrier mobility when being aligned in their mesophase.

The inventive reactive mesogenic compounds are useful as charge transport semiconductors, in that they have high carrier mobilities. In particular, the introduction of side groups to the mesogenic core improves their solubility and therefore their solution processability. In the compounds according to the present invention, the mesogenic core comprises one or more thiophene groups. They are therefore particularly useful as semiconductors or charge transport materials, as they can be processed while in the highly ordered mesophase morphology, and readily aligned by conventional techniques in a preferred direction. Both smectic and nematic mesophase ordering allows close packing of molecular pi-electron systems, which maximises intermolecular charge transfer which occurs through a hopping mechanism between adjacent molecules. This ordered, and oriented microstructure can be permanently "frozen-in" by polymerising the mesogens, which can also create a structure with long range order, or "monodomain". Formation of a monodomain also maximises charge transfer by eliminating charge trap sites at grain boundaries, while the polymerisation also improves the mechanical properties of the film. Further, by cross-linking the mesogens, a highly stable structure results, which has an additional advantage of being impervious to subsequent processing solvents during device fabrication, thus allowing a wider range of solvents to be used in deposition of the next layer of the device by solution techniques. In addition, it is often observed that this cross-linking further densifies the film, leading to smaller intermolecular distances and improved charge transport.

It is also possible to copolymerise the compounds of the present invention with other mesogenic or liquid crystal monomers that are known from prior art, or with other reactive compounds of the present invention, in order to induce or enhance liquid crystal phase behaviour.

Thus, another aspect of the invention relates to a reactive liquid crystal mixture comprising one or more reactive mesogenic compounds of the present invention, and optionally comprising one or more further reactive compounds, which are optionally also mesogenic or liquid crystalline.

Particularly preferred are reactive mesogenic compounds of the present invention, or mixtures comprising one or more reactive mesogenic compounds of the present invention, that exhibit a liquid crystal phase, especially a nematic and/or smectic liquid crystal phase.

Another aspect of invention relates to an anisotropic polymer film with charge transport properties obtainable from a reactive liquid crystal mixture as defined above that is aligned in its liquid crystal phase into macroscopically ordered orientation and polymerised or cross-linked to fix the oriented state.

Another aspect of the invention relates to a liquid crystal side chain polymer (SCLCP) obtained from a reactive liquid crystal material as defined above by polymerisation or polymeranaloguous reaction. Particularly preferred are SCLCPs obtained from one or more reactive mesogenic compounds or mixtures comprising them as described above.

Another aspect of the invention relates to an SCLCP obtained from one or more reactive mesogenic compounds or mixtures as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

The invention also relates to the use of reactive mesogenic compounds of the present invention, or liquid crystal mixtures or polymers obtained thereof, as light-modulating component in liquid crystal displays, which may for example be switchable between two different states by an electric field, for components of liquid crystal displays, in particular optical retardation or compensation films, alignment layers or polarisers, or in other optical or electrooptical devices.

The invention also relates to a liquid crystal display, component of a liquid crystal display, in particular an optical retardation or compensation films, alignment layer or polariser, or an other optical or electrooptical device comprising reactive mesogenic compounds according to the present invention, or liquid crystal mixtures or polymer films obtained thereof.

Very preferred are compounds of formula I wherein
two, three, four, five or six of $A^1$ and $A^2$ are thiophene-2,5-diyl,
two, three or four of $A^1$ and $A^2$ are thiophene-2,5-diyl and two of $A^1$ and $A^2$ are 1,4-phenylene,
at least one, preferably two or more of $A^1$ and $A^2$ are 1,4-phenylene,
all of $A^1$ and $A^2$ are thiophene-2,5-diyl,
$A^1$ and $A^2$ are unsubstituted thiophene or phenylene groups,
R or $R^1$ is H, F, Cl or straight chain, branched or cyclic alkyl with 1 to 20 C-atoms, which is unsubstituted, mono- or polysubstituted by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —$CY^1$=$CY^2$— or —C≡C— in such a manner that O and/or S atoms are not linked directly to one another, or an aromatic or heteroaromatic group, with $Y^1$ and $Y^2$ being independently of one another H, F, Cl or CN,
R or $R^1$ is alkyl or alkoxy with 1 to 15 C atoms which is optionally mono-, poly- or perfluorinated,
R is P—Sp—,
X is —O—, —O—$CH_2$—, —$CH_2$—O— or a single bond,
all groups $Z^1$, $A^1$, $A^2$ and optionally X form a conjugated system,
$Z^1$ is a single bond or a conjugated link such as —$CY^1$=$CY^2$— or —C≡C—,
$Z^1$ is different from —CF=CF—,
one or more, preferably all of $Z^1$ are a single bond,
m is 2, 3, 4 or 5,
m is 3 or 4.
Preferably $A^1$ and $A^2$ are different from

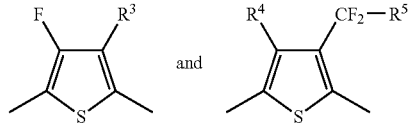

wherein
$R^3$ is straight chain, branched or cyclic alkyl with 1 to 20 C-atoms, which is unsubstituted, mono- or poly-substituted by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl,
$R^4$ is H, F or $R^3$,
$R^5$ is H, straight chain, branched or cyclic alkyl with 1 to 20 C-atoms wherein one or more, but not all, H atoms are optionally replaced by F, Cl, Br, I or CN, and wherein one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, with $R^0$ and $R^{00}$ being as defined in formula I.

A preferred embodiment of the present invention relates to compounds wherein —$A^1$—($Z^1$—$A^2$)$_m$— is selected of formula III1

-Phe-(Z-Thi)$_{m1}$-Z-Phe-     III1 wherein m1 is 2, 3 or 4, the groups Z independently of each other have one of the meanings of $Z^1$ as defined above, Thi is a thiophene-2,5-diyl group and Phe is a 1,4-phenylene group, these groups being optionally substituted by one or more groups $R^1$ as defined above.

Another preferred embodiment of the present invention relates to compounds wherein —$A^1$—($Z^1$—$A^2$)$_m$— is selected of formula II2

-Thi-(Z-Thi)$_m$-      II2 wherein m is as defined in formula I and Z and Thi are as defined in formula II1.

Further preferred groups —$A^1$—($Z^1$—$A^2$)$_m$— are selected of the following formulae and their mirror images -Phe-Z-Thi-Z-Thi-      II3

-Thi-Z-Phe-Z-Thi-      II4

-Phe-Z-Thi-Thi-Thi-      II5

-Phe-Z-Phe-Z-Thi-Z-Thi-      II6

-Thi-Z-Phe-Z-Phe-Z-Thi-      II7

-Phe-Z-Thi-Z-Thi-Z-Thi-Z-Thi-      II8

-Thi-Z-Phe-Z-Thi-Z-Thi-Z-Thi-      II9

-Thi-Z-Thi-Z-Phe-Z-Thi-Z-Thi-      II10

-Phe-Z-Phe-Z-Thi-Z-Thi-Z-Thi-      II11

-Thi-Z-Phe-Z-Phe-Z-Thi-Z-Thi-      II12

-Thi-Z-Phe-Z-Thi-Z-Phe-Z-Thi-      II13

-Phe-Z-Phe-Z-Phe-Z-Thi-Z-Thi-      II14

-Phe-Z-Thi-Z-Phe-Z-Thi-Z-Phe-      II15

-Thi-Z-Phe-Z-Phe-Z-Phe-Z-Thi-      II16

-Phe-Z-Thi-Z-Thi-Z-Thi-Z-Thi-Z-Thi-      II17

-Phe-Z-Phe-Z-Thi-Z-Thi-Z-Thi-Z-Thi-      II18

-Phe-Z-Phe-Z-Phe-Z-Thi-Z-Thi-Z-Thi-      II19

-Phe-Z-Phe-Z-Phe-Z-Phe-Z-Thi-Z-Thi-      II20

-Thi-Z-Thi-Z-Phe-Z-Phe-Z-Thi-Z-Thi-      II21

-Thi-Z-Phe-Z-Phe-Z-Phe-Z-Thi-Z-Thi-      II22

-Thi-Z-Phe-Z-Phe-Z-Phe-Z-Phe-Z-Thi-      II23

-Phe-Z-Phe-Z-Thi-Z-Thi-Z-Phe-Z-Phe-      II24

-Phe-Z-Thi-Z-Phe-Z-Phe-Z-Thi-Z-Phe-      II25

-Thi-Z-Phe-Z-Thi-Z-Thi-Z-Phe-Z-Thi-      II26

-Thi-Z-Thi-Z-Phe-Z-Phe-Z-Thi-Z-Thi-      II27 wherein Z, Thi and Phe have the meanings given above.

Especially preferably Z in formulae II1 to II27 is a single bond.

Particularly preferred are compounds of the following formulae

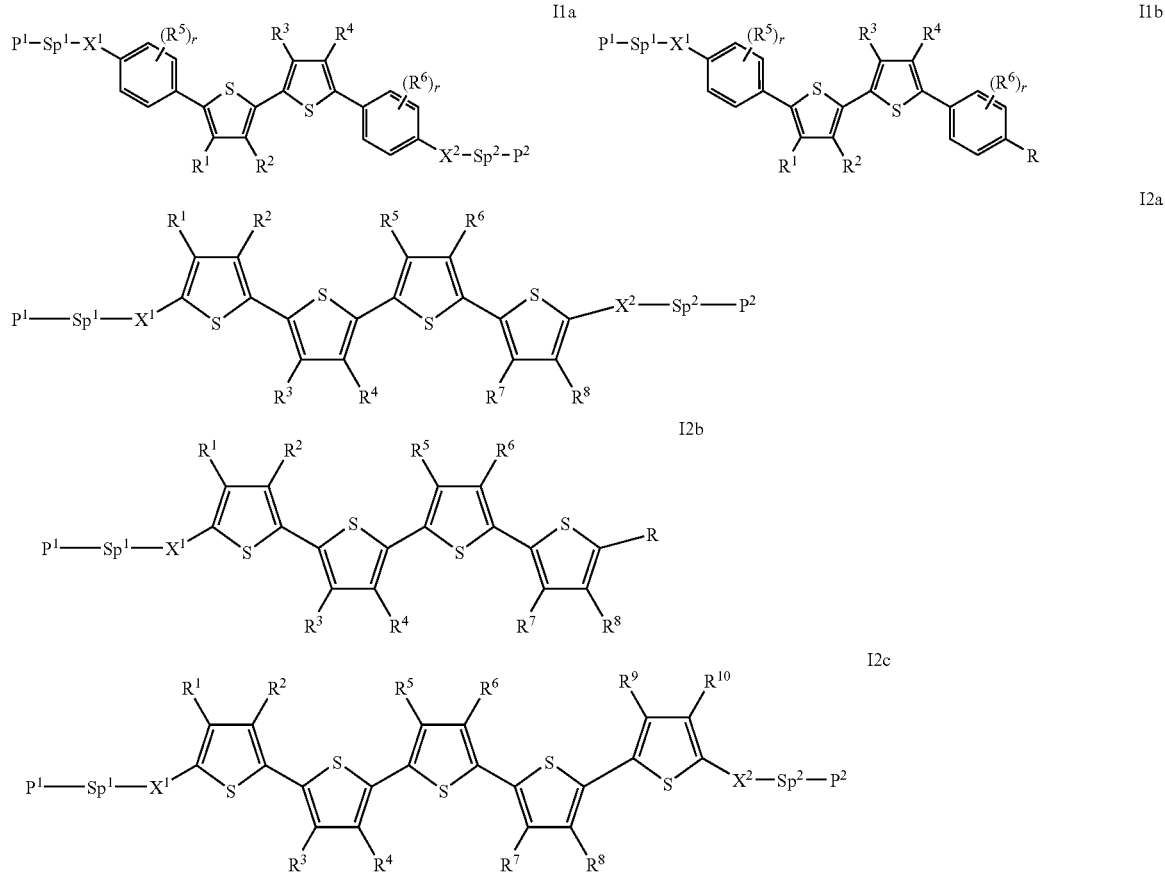

-continued

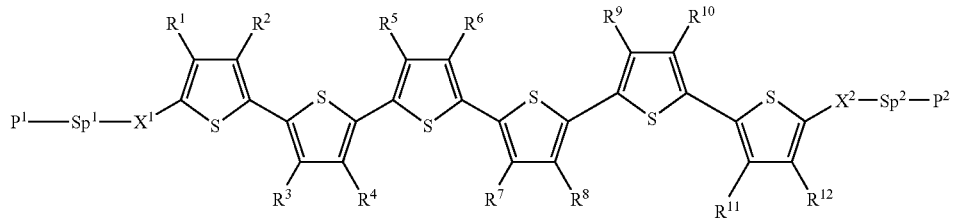
I2d

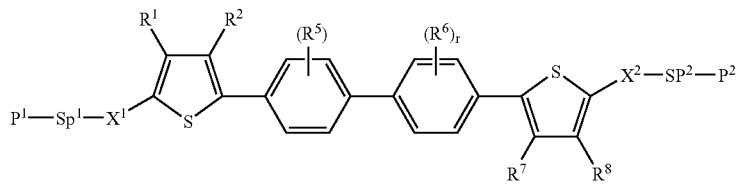
I7a

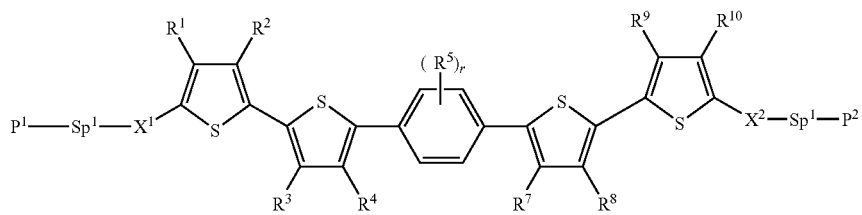
I10a wherein
P¹ and P² are identical or different groups P a defined in formula I,
Sp¹ and Sp² are identical or different groups Sp a defined in formula I,
X¹ and X² are identical or different groups X a defined in formula I,
R is as defined in formula I,
$R^1$ to $R^{12}$ have independently of one another one of the meanings of $R^1$ in formula I, and are preferably H, halogen or straight-chain alkyl with 1 to 8 C-atoms that is optionally mono-, poly- or perfluorinated, and
r is 0, 1, 2, 3 or 4.

Very preferred are the following compounds

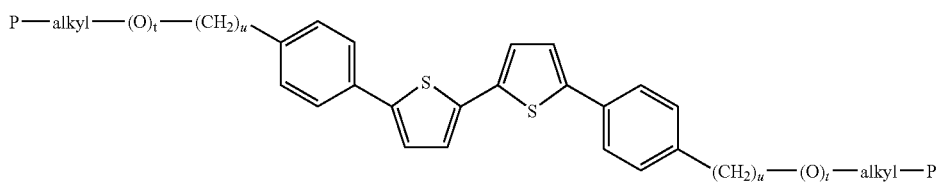
I1a1

I2a1

I2c1

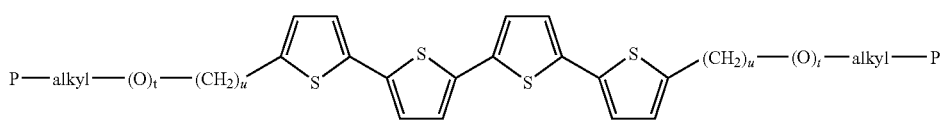

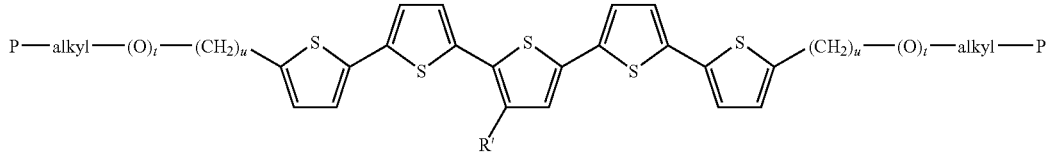
I7a

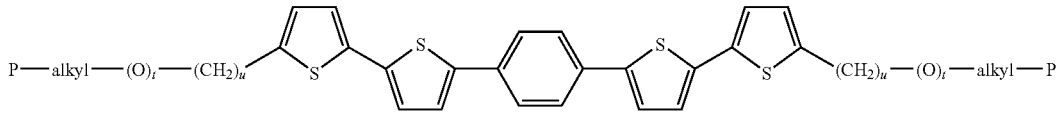

I10a wherein "alkyl" is an alkylene group with 1 to 12, preferably 2 to 8 C-atoms, t is 0 or 1, u is 0 or 1, R' is H or optionally fluorinated $C_{1-8}$-alkyl and P is $CH_2=CW-COO-$,

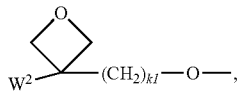

$(CH_2=CH)_2CH-OCO-$ or $(CH_2=CH-CH_2)_2N-CO-$, W is H, $CH_3$, Cl or CN, $W^2$ is H or alkyl with 1 to 5 C-atoms, in particular methyl, ethyl or n-propyl, and k1 is 0 or 1.

$-CY^1=CY^2-$ is preferably $-CH=CH-$, $-CH=CF-$, $-CF=CH-$, $-CF=CF-$, $-CH=C(CN)-$ or $-C(CN)=CH-$.

If one of $R^1$ to $R^{12}$ is an alkyl or alkoxy radical, i.e. where the terminal $CH_2$ group is replaced by $-O-$, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by $-O-$, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

Halogen is preferably F or Cl.

Hetero atoms are preferably selected from N, O and S.

The polymerisable or reactive groups P, $P^1$ and $P^2$ are preferably selected from $CH_2=CW^1-COO-$,

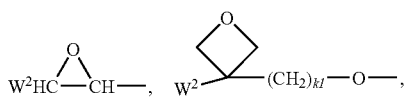

$CH_2=CW^2-(O)_{k1}-$, $CH_3-CH=CH-O-$, $(CH_2=CH)_2CH-OCO-$, $(CH_2=CH-CH_2)CH-OCO-$, $(CH_2=CH)_2CH-O-$, $(CH_2=CH-CH_2)_2N-$, $(CH_2=CH-CH_2)_2N-CO-$, $HO-CW^2W^3-$, $HS-CW^2W^3-$, $HW^2N-$, $HO-CW^2W^3-NH-$, $CH_2=CW^1-CO-NH-$, $CH_2=CH-(COO)_{k1}$-Phe-$(O)_{k2}-$, Phe-CH=CH-, HOOC-, OCN-, and $W^4W^5W^6Si-$, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene that is optionally substituted by one or more groups $R^1$ as defined above, and $k_1$ and $k_2$ being independently of each other 0 or 1.

Especially preferred groups P and $P^{1,2}$ are $CH_2=CH-COO-$, $CH_2=C(CH_3)-COO-$, $CH_2=CH-$, $CH_2=CH-O-$, $(CH_2=CH)_2CH-OCO-$, $(CH_2=CH)_2CH-O-$, $(CH_2=CH-CH_2)_2N-$, $(CH_2=CH-CH_2)_2N-CO-$ and

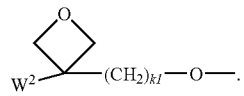

Very preferred are acrylate, methacrylate, diene, $(CH_2=CH)_2CH-OCO-$ and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp, $Sp^1$ and $Sp^2$ all groups can be used that are known for this purpose to those skilled in the art. The spacer group Sp or $Sp^{1,2}$ is preferably a linear or branched alkylene group having 1 to 20 C atoms, in particular 1 to 12 C atoms, in which, in addition, one or more non-adjacent $CH_2$ groups may be replaced by $-O-$, $-S-$, $-NH-$, $-N(CH_3)-$, $-CO-$, $-O-CO-$, $-S-CO-$, $-O-COO-$, $-CO-S-$, $-CO-O-$, $-CH(halogen)-$, $-C(halogen)_2$, $-CH(CN)-$, $-CH=CH-$ or $-C\equiv C-$, or a siloxane group.

Typical spacer groups are for example $-(CH_2)_p-$, $-(CH_2CH_2O)_q-CH_2CH_2-$, $-CH_2CH_2-S-CH_2CH_2-$ or $-CH_2CH_2-NH-CH_2CH_2-$ or $-(SiR^0R^{00}-O)_p-$, with p being an integer from 2 to 12, q being an integer from 1 to 3 and $R^0$ and $R^{00}$ having the meanings given in formula I.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

The linkage group X, $X^1$ and $X^2$ preferably denotes $-O-$, $-S-$, $-OCH_2-$, $-CH_2O-$, $-CO-$, $-COO-$, $-OCO-$, $-OCO-O-$, $-CO-NR^0-$, $-NR^0-CO-$, $-O-CO-NR^0-$, $-NR^0-CO-O-$, $-NR^0-CO-NR^0-$, $-OCH_2-$, $-CH_2O-$, $-SCH_2-$, $-CH_2S-$, $-CH=CH-COO-$, $-OOC-CH=CH-$, $-CF_2O-$, $-OCF_2-$, $-CF_2S-$, $-SCF_2-$, $-CH_2CH_2-$, $-CF_2CH_2-$, $-CH_2CF_2-$, $-CF_2CF_2-$, $-CH=N-$, $-N=CH-$, $-N=N-$, $-CH=CR^0-$, $-CY^1=CY^2-$, $-C\equiv C-$ or a single bond, with $R^0$, $Y^1$ and $Y^2$ having the meanings given above.

In a preferred embodiment, the linkage group X, $X^1$ or $X^2$ is an unsaturated group that is capable of forming a conjugated system, such as —CH=N—, —N=CH—, —N=N—, —CH=$CR^0$—, —$CY^1$=$CY^2$—, —C≡C—, or a single bond.

Further preferred are compounds with one or two groups P—Sp—X wherein Sp and/or X is a single bond.

In case of compounds with two or more groups P—Sp—X, each of the groups P, the groups Sp, and the groups X can be identical or different.

SCLCPs obtained from the inventive compounds or mixtures by polymerisation or copolymerisation have a backbone that is formed by the polymerisable group P in formula I.

The compounds of formula I can be synthesized according to or in analogy to methods that are known to the skilled in the art and are reported in the literature. Furthermore, they can be prepared according to or in analogy to the following reaction schemes.

Scheme 1:

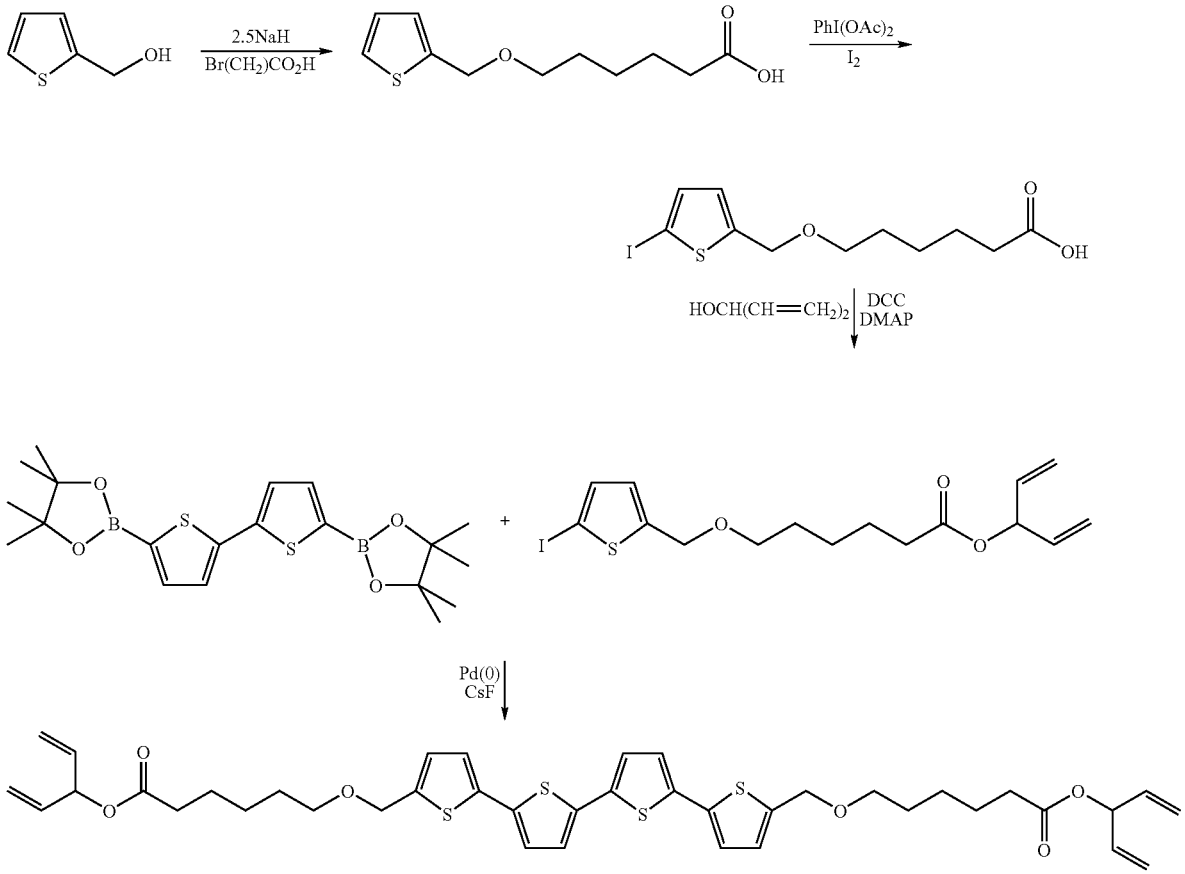

Scheme 2:

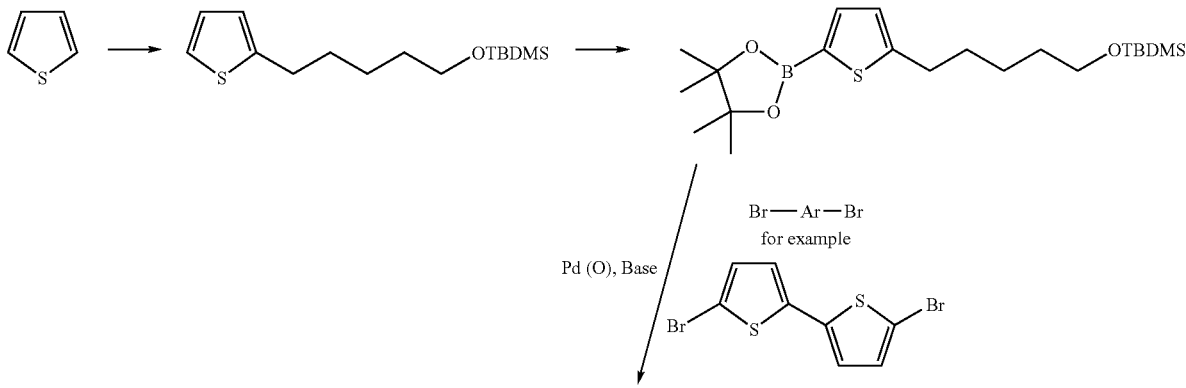

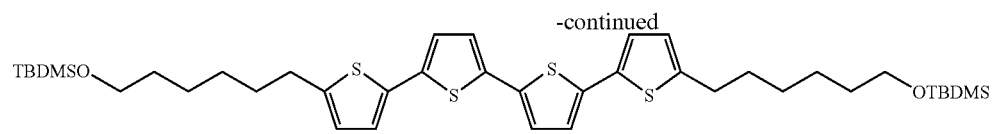
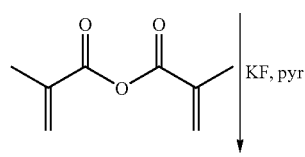
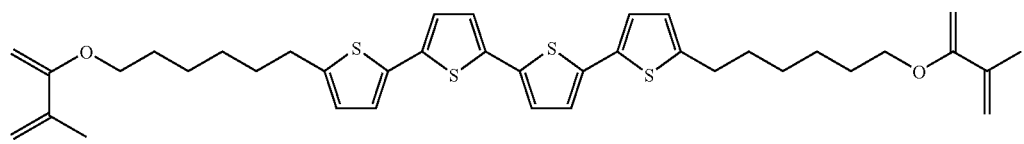
Scheme 3:
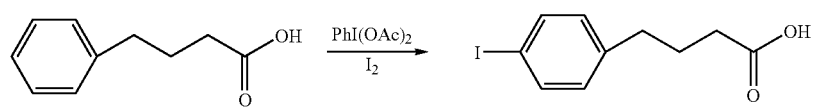
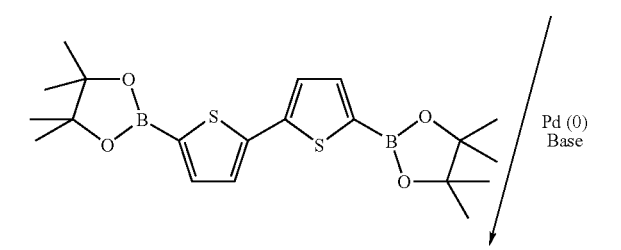
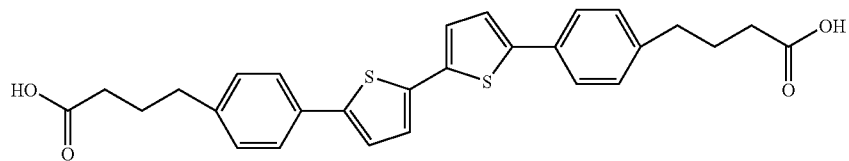
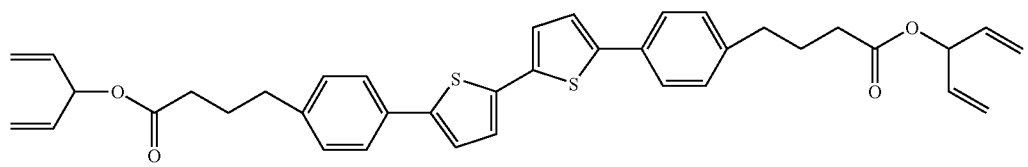

As outlined in scheme 1-3, compounds of formula I can be synthesised by transition metal catalysed cross-coupling methodologies. A convenient procedure is the Suzuki reaction involving aryl boronic acids, however the present compounds can also be synthesised by the transition metal catalysed coupling of organotins (Stille reaction), organozincs (Negishi coupling), organomagnesiums (Kumada coupling), organosilicon reagents or aryl lithiums. The polymerisable endgroups can be incorporated before the cross-coupling step (scheme 1), or afterwards (scheme 2 or 3).

The reactive mesogenic compounds of formula I are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

It is also possible to copolymerise the compounds according to the present invention with other polymerisable mesogenic or liquid crystal monomers that are known from prior art, in order to induce or enhance liquid crystal phase behaviour.

Thus, another aspect of the invention relates to a polymerisable liquid crystal material comprising one or more reactive mesogenic compounds of the present invention as described above and below comprising at least one polymerisable group, and optionally comprising one or more further polymerisable compounds, wherein at least one of the reactive mesogenic compounds of the present invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred. Especially preferred are smectic A ($S_A$) phases, furthermore highly ordered smectic phases like the $S_B$, $S_E$, $S_G$ and $S_F$ phase.

Another aspect of the invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Polymerisation is preferably carried out by in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45-66.

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Polymerisable benzodithiophenes comprising one or more groups P—Sp—X can also be copolymerised with polymerisable mesogenic compounds to induce, or, in case of mesogenic materials of formula I, enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

SCLCPs can be prepared from the polymerisable compounds or mixtures according to the invention by the methods described above, or by conventional polymerisation techniques which are known to those skilled in the art, including for example radicalic, cationic or anionic polymerisation from unsaturated functionality radicalic, polyaddition or polycondensation. Polymerisation can be carried out for example as polymerisation in solution, without the need of coating and prior alignment, or polymerisation in situ.

It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added e.g. to polysiloxane backbones with Si—H groups.

It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397; EP 0,261,712; DE 195,04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

For example, if a device is made from a polymerisable liquid crystal material by polymerisation in situ, the liquid crystal material preferably comprises one or more compounds of formula I and its preferred subformulae having one or more groups P. If a liquid crystal polymer is prepared first, for example by polymerisation in solution, and the isolated polymer is used to make the device, the polymer is preferably made from a liquid crystal material comprising one or more compounds of formula I and its preferred subformulae having one group P.

The materials of the present invention are useful as optical, electronic and semiconductor materials, in particular as charge transport materials in field effect transistors (FETs) e.g. as components of integrated circuitry, ID tags or TFT applications. Alternatively, they may be used in organic light emitting diodes (OLEDs) in electroluminescent display applications or as backlight of e.g. liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques e.g. spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known e.g. from U.S. Pat. No. 5,892, 244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Alternatively, the materials according to the invention may be used in organic light emitting devices or diodes (OLEDs), e.g. in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e.g. Meerholz, Synthetic Materials, 111-112, 2000, 31-34, Alcala, J. Appl. Phys., 88, 2000, 7124-7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279, 1998, 835-837.

The materials of the present invention are also useful for the preparation of optical films with anisotropic properties, like for example polarizers, optical retardation films, compensators, colour filters, polarization beam splitters, or polarization filters, which can be used for example as components of liquid crystal displays. Furthermore, they can be used as coatings e.g. for decorative or security use, as adhesives, or for the preparation of liquid crystal pigments.

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$).

When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, $R_4P^+$, $R_6As^+$, and $R_3S^+$ (wherein R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns of tracts in electronic applications such as printed circuit boards and condensers.

The entire disclosures of all applications, patents and publications mentioned hereinbefore and hereinafter and of U.S. 60/547,068 filed Feb. 25, 2004 and EP 04005797.8 filed Mar. 11, 2004 are incorporated into this application by reference.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

The examples below serve to illustrate the invention without limiting it. In the foregoing and the following, all temperatures are given in degrees Celsius, and all percentages are by weight, unless stated otherwise. $S_x$ and $S_{x1}$ refer to smectic liquid crystal phases of undetermined structure.

Example 1

Compound (1) is prepared as follows:

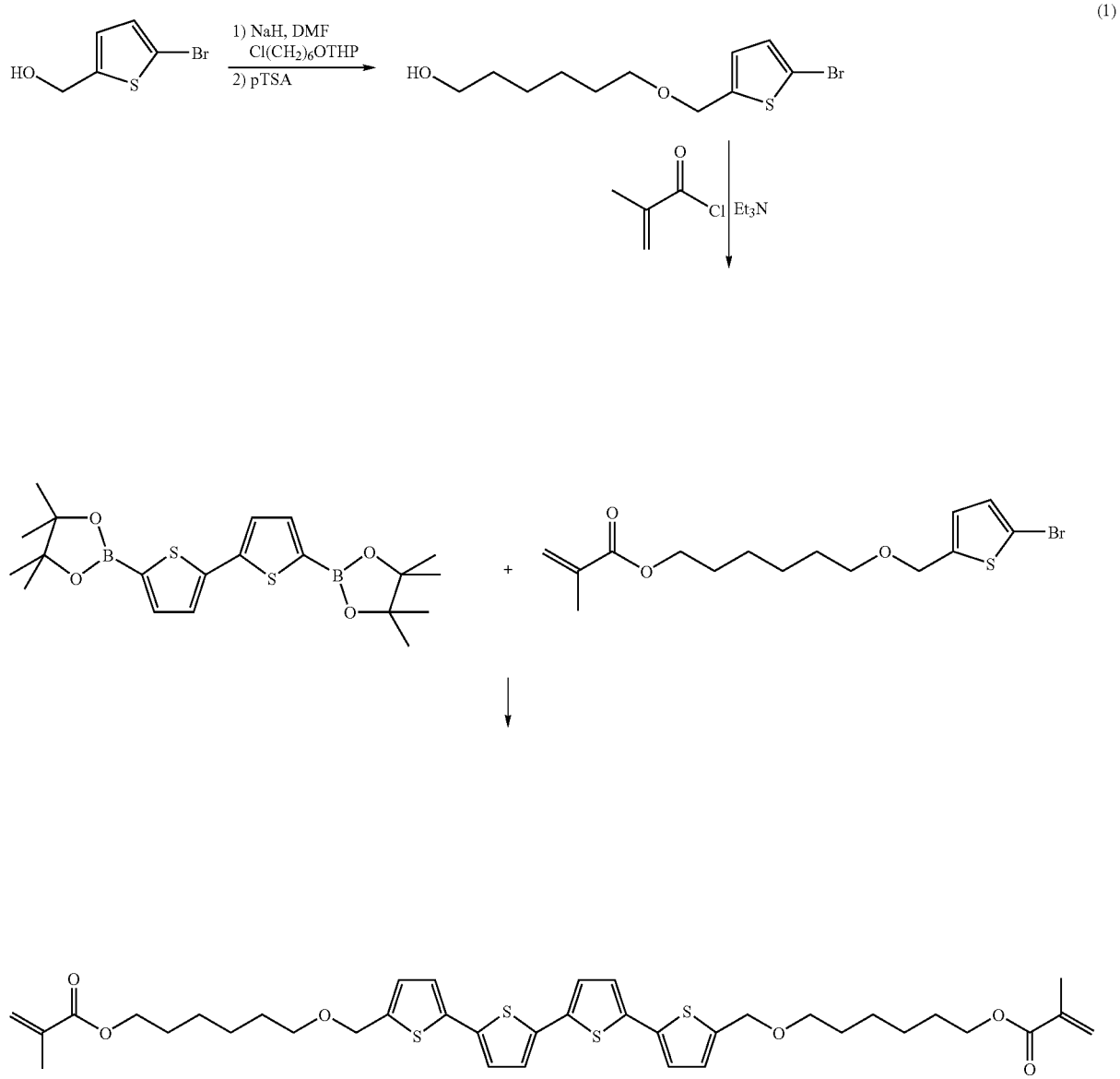

(1)

Step 1.1: 6-[(5-bromothiophen-2-yl)methoxy]hexan-1-ol

5-Bromo-2-thiophene methanol (2.93 g, 15.1 mmol) is added to a suspension of sodium hydride (60% w/w dispersion in mineral oil, 0.60 g, 15.1 mmol) in anhydrous DMF (25 mL) at 0° C., under nitrogen, with stirring. After 10 min, 2-(6-chlorohexyloxy)tetrahydro-2H-pyran (3.33, 15.1 mmol, Aldrich) is added dropwise. This mixture is stirred overnight at room temperature, then quenched with water (50 mL) and extracted with ethyl acetate (3×40 mL). The extracts are washed with water (40 mL) and brine (40 mL), dried ($Na_2SO_4$), and evaporated under reduced pressure. The residue is purified by column chromatography on silica, eluting with petroleum ether (40-60° C.)/ethyl acetate (from 90:10 to 70:30) to afford the product as a pale yellow oil. This is dissolved in methanol (70 mL), followed by the addition of p-toluenesulphonic acid (0.5 g). This mixture is heated at 35° C. for 6h, then concentrated under reduced pressure. The residue is treated with sat. aq. $NaHCO_3$ solution (50 mL), then extracted with ethyl acetate (3×50 mL). The extracts are washed with water (50 mL) and brine (50 mL), dried ($Na_2SO_4$), and evaporated under reduced pressure. The product is purified by column chromatography on silica, eluting with petroleum ether (40-60° C.)/ethyl acetate (70:30) to give the product as a pale yellow oil (3.51 g). NMR and MS showed the expected signals.

Step 1.2: 2-Methylacrylic acid (5-bromothiophen-2-yl)methoxyhexyl ester

Triethylamine (2.10 g, 20.8 mmol) is added dropwise to a solution of 6-(5-bromothiophen-2-yl)methoxyhexanol (3.10 g, 10.62 mmol) and methacryloyl chloride (1.20 g, 11.54 mmol) in DCM (30 mL) at −10° C. This mixture is allowed to warm to room temperature and stirred overnight before it is quenched by the addition water (50 mL) The organic layer is separated and the liquid phase is extracted with DCM (2×30 mL). The organic layers is combined, washed with brine (50 mL), dried ($Na_2SO_4$) and evaporated under reduced pressure. The product is purified by column chromatography on silica, eluting with petroleum ether (40-60° C.)/ethyl acetate (90:10) to afford the product as a pale yellow oil (3.27 g, 86%). NMR and MS showed the expected signals.

Step 1.3: 2-Methacrylic acid 6-{5'''-[5-(2-methylacryloyloxy)-hexyloxymethyl][2,2';5',2'';5'',2''']quaterthiophen-5-ylmethoxy}hexyl ester (1)

Tetrakis(triphenylphosphine)palladium(0) (0.05 g) is added to a solution of 2-methylacrylic acid (5-bromothiophen-2-yl)methoxyhexyl ester (0.50 g, 1.38 mmol) in dry DME (50 mL) with stirring under nitrogen. After 20 min, 5,5'-di(4,4,5,5-tetramethyl[1,3,2]dioxoborolan-2-yl)-2,2'-bithiophene (0.21 g, 0.5 mmol, see M. Melucci, G. Barbarella, G. Sotgiu *J. Org. Chem.* 2002, 67, 8877) is added, followed by cesium fluoride (0.30 g, 2.0 mmol) and 2,6-di-tert-butyl-4-methylphenol (0.05 g). The reaction mixture is heated under reflux for 15 h. After cooling, water (50 mL) is added, followed by extraction with ethyl acetate (3×50 mL). The combined extracts are washed with water (50 mL), brine (50 mL), dried ($Na_2SO_4$), filtered and evaporated under reduced pressure. The crude residue is purified by column chromatography on silica, eluting with petroleum ether (40-60° C.)/diethyl ether (90:10 to 80:20), to give a yellow solid, which is recrystallized from ethyl acetate to afford 1 as yellow crystals (0.16 g, 0.43%): $^1$H NMR ($CDCl_3$, 300 MHz): δ 7.08 (m, 4H), 7.03 (d, $^3J$=3.6 Hz, 2H), 6.89 (d, $^3J$=3.6 Hz, 2H) 6.11 (br s, 2H, =CH), 5.55 (br s, 2H, =CH), 4.63 (s, 4H), 4.15 (t, $^3J$=6.6 Hz, 4H), 3.51 (t, $^3J$=6.6 Hz, 4H), 1.95 (s, 6H), 1.67 (m, 8H), 1.42 (m, 8H); $^{13}$C NMR ($CDCl_3$, 75 MHz): δ 167.9 (C=O), 141.3, 137.7, 136.9, 136.8, 136.2, 127.3, 125.6, 124.7, 124.6, 123.6, 70.5, 67.9, 65.1, 30.0, 29.0, 26.4, 26.3, 18.8; MS (ESI$^+$): m/e 766 ((M+K)$^+$, 33%); IR (powder): ν (cm$^{-1}$) 1709 (C=O), 1169 (C—O). m.p. (°) K 84 $S_{CryB}$ 101 I.

Example 2

Compound (2) is prepared as follows:

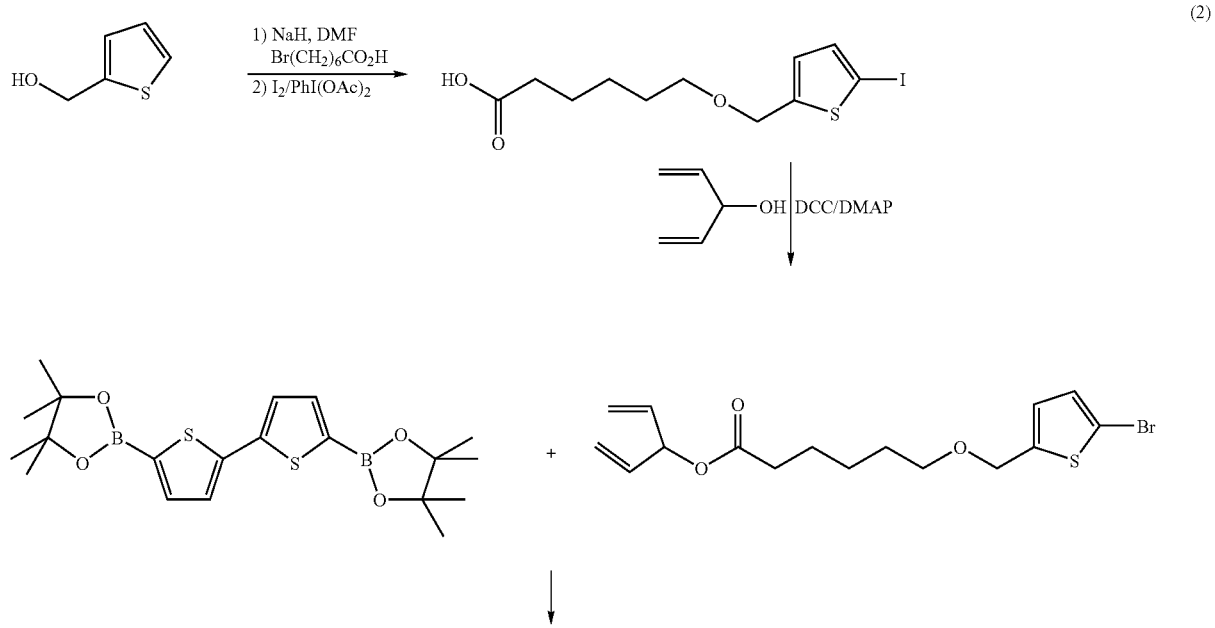

-continued

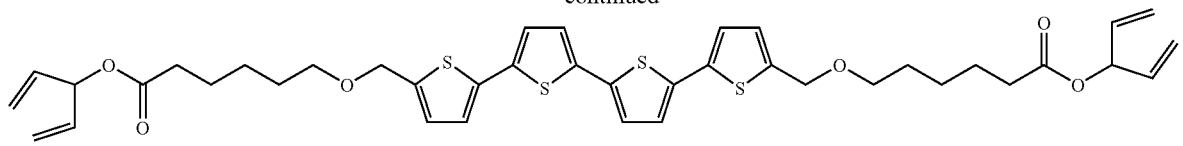

Step 2.1: 6-(5-Iodo-thiophen-2-ylmethoxy)hexanoic acid

To a suspension of sodium hydride (60% w/w dispersion in mineral oil, 4.56 g, 0.114 mol) in anhydrous DMF (250 mL) at 0° C. under nitrogen, is added 6-bromohexanoic acid (10.0 g, 51.3 mmol) in portions over 15 min. The mixture is stirred for 30 min, followed by the dropwise addition of thiophene-2-methanol (7.10 g, 62.2 mmol). The resulting cloudy solution is allowed to warm to room temperature and stirred for 48 h before it is quenched by pouring into water (250 mL). Diethyl ether (200 mL) is added and the layers are separated and the organic phase is discharged. The water phase is acidified with 6 M HCl solution and extracted with ethyl acetate (3×150 mL). The combined extracts are washed with water (150 mL), brine (2×100 mL), dried ($Na_2SO_4$), filtered and evaporated under reduced pressure. The residue is purified by column chromatography on silica, eluting with petroleum ether/ethyl acetate (4:1 to 3:2) to give the product as a light brown oil (9.73 g). This is dissolved in DCM (150 mL) in the absence of light, and iodobenzene diacetate (6.75 g, 21.0 mmol) is added, followed by iodine (5.33 g, 21.0 mmol) in portions. The reaction mixture is stirred for 4 h at room temperature and then washed with sat. aq. sodium metabisulphite (100 mL), water (100 mL), brine (2×50 mL), dried ($Na_2SO_4$), filtered and evaporated under reduced pressure. The residue is dissolved in 10% NaOH solution (100 mL) and then washed with diethyl ether (3×50 mL) to remove iodobenzene. The aqueous layer is acidified with 6M HCl solution and extracted with ethyl acetate (3×70 mL). The combined organics are washed with water (70 mL), brine (100 mL), dried ($Na_2SO_4$), filtered and concentrated under reduced pressure. Further purification by column chromatography on silica, eluting with petroleum ether/ethyl acetate (70:30) afforded the product as a brown oil (13.72 g). NMR showed the expected signals.

Step 2.2: 6-(5-Iodo-thiophen-2-ylmethoxy)hexanoic acid 1-vinyl-allyl ester

A mixture of 6-[5-iodo-(2-thienyl)]methoxyhexanoic acid (13.20 g, 37.3 mmol), 1,4-pentadien-3-ol (3.13 g, 37.3 mmol), dicyclohexylcarbodiimide (7.70 g, 37.3 mmol) and 4-dimethylaminopyridine (0.1 g) in DCM (250 mL) is stirred for 12 h under nitrogen. The solid is removed by filtration and the filtrate is evaporated under reduced pressure. The residue is purified by column chromatography on silica, eluting with petroleum ether/diethyl ether (90:10), to give the product as a brown oil (12.27 g, 77%) NMR showed the expected signals.

Step 2.3: 6-{5'''-[5-(1-vinylallyloxycarbonyl)pentyloxymethyl]-[2,2':5'',2''':5''',2''']-quarterthiophen-5-ylmethoxy}hexanoic acid 1-vinylallyl ester (2)

Tetrakis(triphenylphosphine)palladium(0) (0.1 g, 0.1 mmol) is added to a solution of 6-(5-iodo-thiophen-2-ylmethoxy)hexanoic acid 1-vinyl-allyl ester (0.50 g, 1.2 mmol) in dry degassed DME (70 mL) with stirring under nitrogen. After 20 min, 5,5'-di(4,4,5,5-tetramethyl[1,3,2]dioxoborolan-2-yl)-2,2'-bithiophene (0.21 g, 0.5 mmol) is added, followed by cesium fluoride (0.30 g, 2.0 mmol). The reaction mixture is heated under reflux for 12 h. After cooling, water (50 mL) is added, followed by extraction with ethyl acetate (3×50 mL). The combined extracts are washed with water (50 mL), brine (50 mL), dried ($Na_2SO_4$), filtered and evaporated under reduced pressure. The crude residue is purified twice by column chromatography on silica, eluting with petroleum ether/diethyl ether (90:10 to 80:20), to give a yellow solid, which is recrystallized from 2-propanol to afford the product as yellow crystals (0.17 g, 45%): $^1$H NMR (CDCl$_3$, 300 MHz): δ 7.07 (m, 4H, Ar—H), 7.03 (d, $^3J$=3.60 Hz, 2H), 6.89 (d, $^3J$=3.60 Hz, 2H), 5.80-5.91 (m, 4H, =CH), 5.73 (m, 2H, O—CH), 5.22-5.34 (m, 8H, =CH$_2$), 4.64 (s, 4H, Ar—CH$_2$—O), 3.52 (t, $^3J$=6.5 Hz, 4H, O—CH$_2$), 2.38 (t, $^3J$=7.6 Hz, 4H, CH$_2$—CO), 1.67 (m, 8H,), 1.45 (m, 4H). $^{13}$C NMR (CDCl$_3$, 75 MHz): δ 172.97 (C=O), 141.27, 137.70, 136.76, 136.24, 135.55, 127.30, 124.68, 124.65, 123.58, 117.80, 75.24, 70.33, 67.90, 34.84, 29.74, 26.11, 25.16. MS (ESI$^+$): m/e 768 (M$^+$+17, 38%), 279 (100). IR (powder): ν (cm$^{-1}$) 1731 (C=O). Anal. Calcd for $C_{40}H_{46}O_6S_4$: C, 63.97; H, 6.17; S, 17.08. Found: C, 63.9; H, 5.7; S, 17.1. m.p. (° C.) K 0 S$_H$ 56 S$_G$ 98 I.

Example 3

Compound (3) is prepared as follows:

(3)

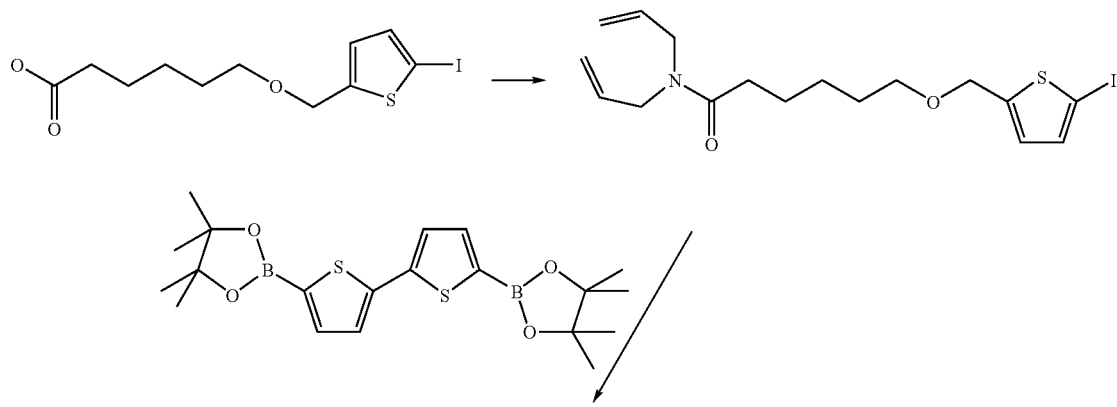

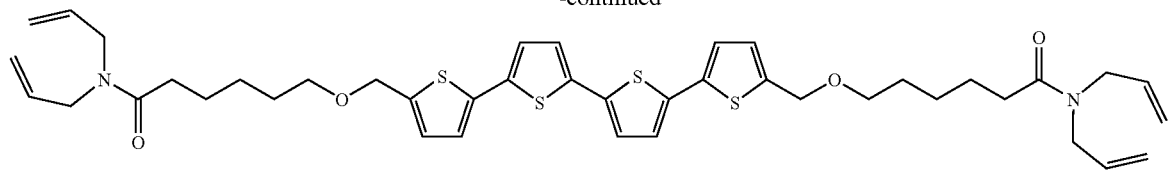

Step 3.1: 6-(5-Iodo-2-thiophen-2-ylmethoxy)-hexanoic acid N,N-diallylamide

A mixture of 6-[5-iodo-(2-thienyl)]methoxyhexanoic acid (5.0 g, 14.12 mmol), diallylamine (1.37 g, 14.12 mmol), dicyclohexyl-carbodiimide (2.91 g, 14.12 mmol) and 4-dimethylaminopyridine (0.1 g) in DCM (70 ml) is stirred for 12 h. The solid is removed by filtration and the filtrate is evaporated under reduced pressure. The residue is purified by column chromatography on silica, eluting with petroleum ether/ethyl acetate (from 5:1 to 3:1), to afford the product as a brown oil (5.13 g). $^1$H NMR (300 Hz, CDCl$_3$): δ (ppm) 7.07 (d, J=3.6 Hz, 1H, Ar—H), 6.64 (d, J=3.6 Hz, 1H, Ar—H), 5.75 (m, 2H, =CH), 5.14 (m, 4H, =CH$_2$), 4.58 (s, 2H, OCH$_2$), 3.97 (d, J=5.8 Hz, 2H, NCH$_2$), 3.86 (d, J=4.7 Hz, 2H, NCH$_2$), 3.45 (t, J=6.6 Hz, 2H, OCH$_2$), 2.30 (t, J=7.6 Hz, 2H, COCH$_2$), 1.62 (m, 4H, CH$_2$), 1.38 (m, 2H, CH$_2$).

Step 3.2: 6-[5'''-(Diallylcarbamoyl-pentyloxymethyl)-[2,2';5',2'';5'',2''']quaterthiophen-5-ylmethoxy]-hexanoic acid diallylamide Tetrakis(triphenylphosphine)palladium(0) (0.10 g, 0.1 mmol) is added to a solution of 6-(5-iodo-2-thiophen-2-ylmethoxy)-hexanoic acid N,N-diallylamide (0.63 g, 1.45 mmol) in dry DME (50 ml) with stirring under nitrogen. After 20 min, 5,5'-di(4,4,5,5-tetramethyl[1,3,2]dioxoborolan-2-yl)-2,2'-bithiophene (0.20 g, 0.48 mmol) is added, followed by the addition of cesium fluoride (0.30 g, 2.0 mmol). The reaction mixture is heated at reflux for 3 h under nitrogen. After cooling, water (30 ml) is added, followed by extraction with ethyl acetate (3×50 ml). The extracts are washed with water (50 ml) and brine (50 ml), dried (Na$_2$SO$_4$) and evaporated under reduced pressure. Purification by column chromatography on silica, eluting with petroleum ether/ethyl acetate (from 5:2 to 2:1), gave a yellow solid, which is recystallised twice from ethyl acetate to afford 3 as yellow crystals (0.19 g, 51%). $^1$H NMR: δ (ppm) 7.03 (m, 6H, Ar—H), 6.87 (d, J=3.6 Hz, 2H, Ar—H), 5.74 (m, 4H, =CH), 5.15 (m, 8H, =CH$_2$), 4.61 (s, 4H, OCH$_2$), 3.99 (d, J=5.8 Hz, 4H, NCH$_2$), 3.85 (d, J=4.3 Hz, 4H, NCH$_2$), 3.50 (t, J=6.6 Hz, 4H, OCH$_2$), 2.31 (t, J=7.7 Hz, 4H, COCH$_2$), 1.65 (m, 8H, CH$_2$), 1.41 (m, 4H, CH$_2$). m.p. (° C.) K 48 S$_x$ 72 I.

Example 4

Compound (4) is prepared as follows:

(4)

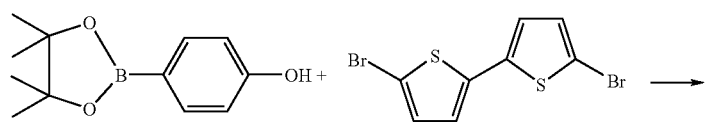

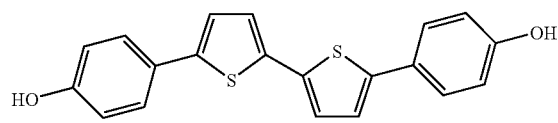

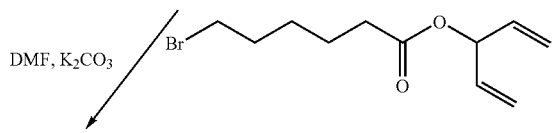

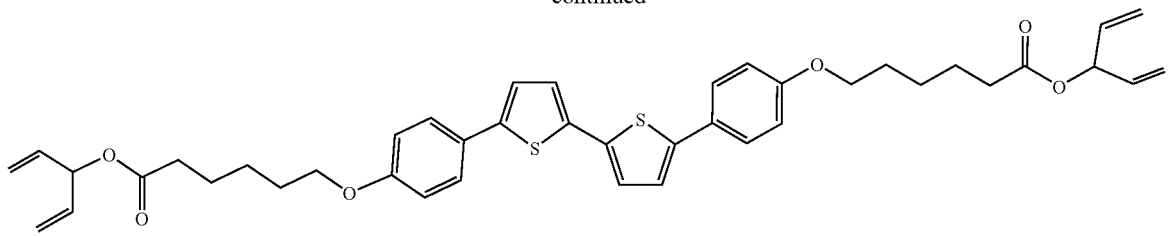

Step 4.1: 2,5'-Bis(4-hydroxyphenyl)bithiophene

To a solution of 5,5'-dibromo-2,2'-bithiophene (5.0 g, 15.43 mmol) in anhydrous THF (120 ml) is added tetrakis(triphenylphosphine) palladium (0.5 g, 0.43 mmol). This mixture is degassed with nitrogen for 20 min followed by the addition of 4-(4,4,5,5-tetramethyl[1,3,2]dioxoborolan-2-yl)-phenol (3.73 g, 16.95 mmol, Aldrich) and tetraethylammonium hydroxide (20% solution in water, 50 ml). The mixture is heated at reflux for 5 h. After cooling, 1M HCl solution (70 ml) is added and the precipitate is filtered off then washed with water (3×20 ml) and dried, to give a green solid (4.52 g, 84%). NMR showed the expected signals.

Step 4.2: 6-[4-(5'-{4-[5-(1-vinyl-allyloxycarbonyl)-pentyloxy]-phenyl}-[2,2']bithiophenyl-5-yl)-phenoxy]-hexanoic acid 1-vinyl-allyl ester 2,5'-Bis(4-hydroxyphenyl)bithiophene (0.50 g, 1.43 mmol) is dissolved in DMF (50 ml), followed by the addition of potassium carbonate (0.59 g, 4.29 mmol), 6-bromohexanoic acid 1-vinylallyl ester (1.12 g, 4.29 mmol, see A. E. A. Contoret et al, *Chem. Mater.* 2002, 14, 1477) and potassium iodide (0.71 g, 4.29 mmol). This mixture is stirred overnight at 70° C. under nitrogen. After cooling, water (100 ml) is added, followed by extraction with ethyl acetate (3×70 ml). The organic phases are combined, dried and evaporated under reduced pressure. The residue is purified by column chromatography on silica, eluting with petrol/ethyl acetate (4:1 to 7:3), to give a yellow solid, which is recrystallised from ethyl acetate to give yellow crystals (0.39 g, 41%). $^1$H NMR (300 MHz, CDCl$_3$): δ (ppm) 7.51 (d, 4H), 7.10 (s, 4H), 6.89 (d, 4H), 5.84 (m, 4H, =CH), 5.73 (m, 2H), 5.25 (m, 8H, =CH$_2$), 3.95 (t, 4H), 2.40 (t, 4H), 1.51-1.90 (m, 8H), 1.25 (m, 4H); $^{13}$C NMR (75 MHz, CDCl$_3$): δ (ppm) 172.5 (2×C=O), 158.8 (2×quat.), 143.0 (2×quat.), 135.8 (2×quat.), 135.2 (2×quat. and 4×CH), 126.9 (4×CH), 124.2 (2×CH), 122.7 (2×CH), 117.5 (4×CH$_2$), 114.9 (4×CH), 74.9, 67.75, 34.4, 29.0, 25.7, 24.7. m.p. (° C.) K 135 S$_G$ 187 S$_C$ 196 I.

Example 5

Compound (5) is prepared as follows

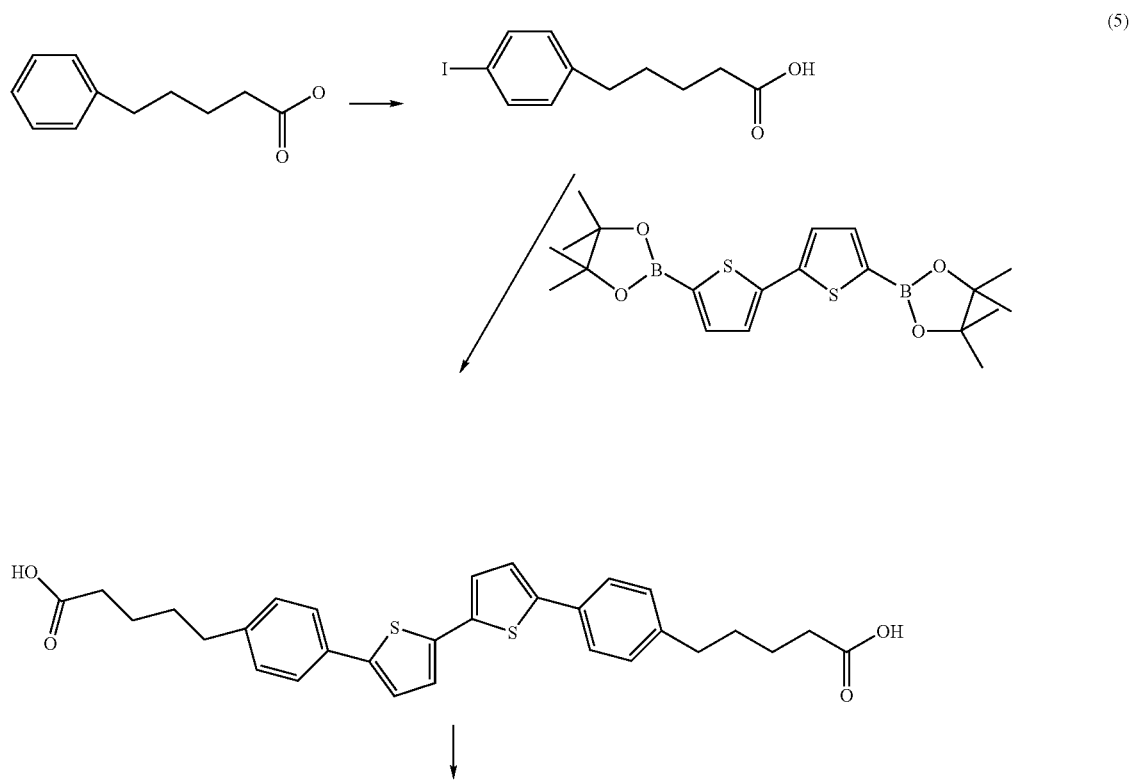

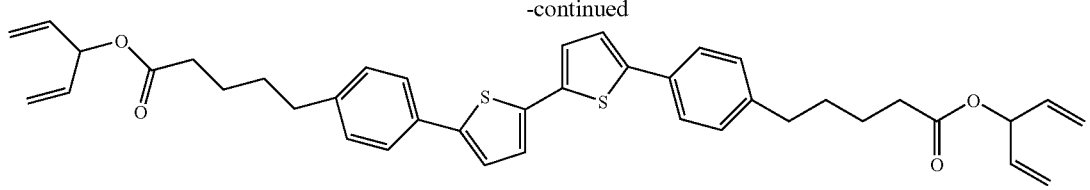

Step 5.1: 5-(4-Iodophenyl)pentanoic acid

5-Phenylpentanoic acid (50.0 g, 0.28 mol), iodine (37.77 g, 0.149 mol) and (diacetoxyiodo)benzene (48.0 g, 0.149 mol) are suspended in a mixture of glacial acetic acid (500 mL) and acetic anhydride (500 mL). Concentrated sulfuric acid (2 mL) is added and the suspension stirred for 2 h in the dark, during which the red colour fades. The solvent is removed under reduced pressure until approximately 80 ml remained, and the residue poured into ice-water (1 L) containing sodium metabisulfite (8 g). the resulting precipitate is stirred for 30 min, and then filtered. The crude product is recrystallised from ethanol/water, and then from acetic acid/water to afford the product (58.5 g). NMR showed the expected signals.

Step 5.2: 5-(4-{5'-[4-(4-Carboxy-butyl)-phenyl]-[2,2']bithiophenyl-5-yl}-phenyl)-pentanoic acid 5-(4-Iodophenyl)pentanoic acid (2.64 g, 8.68 mmol) and 5,5'-di(4,4,5,5-tetramethyl[1,3,2]dioxoborolan-2-yl)-2,2'-bithiophene (1.54 g, 3.69 mmol) are dissolved in anhydrous NMP (70 ml) at room temperature under nitrogen. Tetrakis(triphenylphosphine)palladium (0) (107 mg, 0.09 mmol) is added and the mixture warmed to 40° C. Tetrabutylammonium hydroxide (10 mL of a 40 wt. % solution in water) is added and the mixture heated to 110° C. for 16 h. The reaction is cooled to room temperature and poured into an ice-cold aqueous solution of 5% HCl (500 ml). The resulting precipitate is filtered, and triturated with water, methanol and acetone to afford 1.96 g of product. NMR showed the expected signals.

Step 5.3: 5-[4-(5'-{4-[4-(1-Vinyl-alloxycarbonyl)-butyl]-phenyl}-[2,2']bithiophenyl-5-yl)-phenyl]-pentanoic acid 1-vinyl-allyl ester (5)

5-(4-{5'-[4-(4-Carboxy-butyl)-phenyl]-[2,2']bithiophenyl-5-yl}-phenyl)-pentanoic acid (1.05 g, 2.02 mmol) and 1,4-pentadien-3-ol (0.42 g, 5.0 mmol) are suspended in NMP (52 mL). 1-(3-Dimethlaminopropyl)-3-ethylcarbodiimide hydrochloride [EDCI] (0.96 g, 5.0 mmol) is added, followed by 4-dimethylaminopyridine (0.61 g, 4.9 mmol) and the mixture is warmed to 50° C. for 10 min. The resulting solution is stirred at room temperature for 3 days. The mixture is poured into water (300 ml) and the resulting precipitate filtered. The solid is dissolved in THF (300 mL), filtered and dry loaded onto silica. The silica is loaded onto a dry silica column and eluted with petrol/dichloromethane (4:1) to remove non-coloured products. The eluent is changed to chloroform and the coloured fractions are collected to afford crude product (1.06 g). A portion (0.5 g) is further purified by reverse phase chromatography (eluent: acetonitrile/THF 9:1 to 1:1, gradient). Final recrystallisation from ethyl acetate afforded the product (0.15 g). $^1$H NMR (300 MHz, CDCl$_3$): δ (ppm) 7.51 (d, 4H), 7.20 (s, 4H), 7.14 (d, 4H), 5.83 (m, 4H), 5.71 (m, 2H), 5.25 (m, 8H), 2.64 (t, 4H), 2.38 (t,0 4H), 1.73-1.63 (m, 8H); $^{13}$C NMR (75 MHz, CDCl$_3$): δ (ppm) 172.4, 143.2, 142.8, 136.4, 135.2, 129.0, 125.6, 125.5, 124.4, 123.4, 117.4, 74.9, 34.9, 34.0, 30.1, 25.9. m.p. (° C.) K 75 S$_X$ 174 I.

Example 6

Compound (6) is prepared as follows:

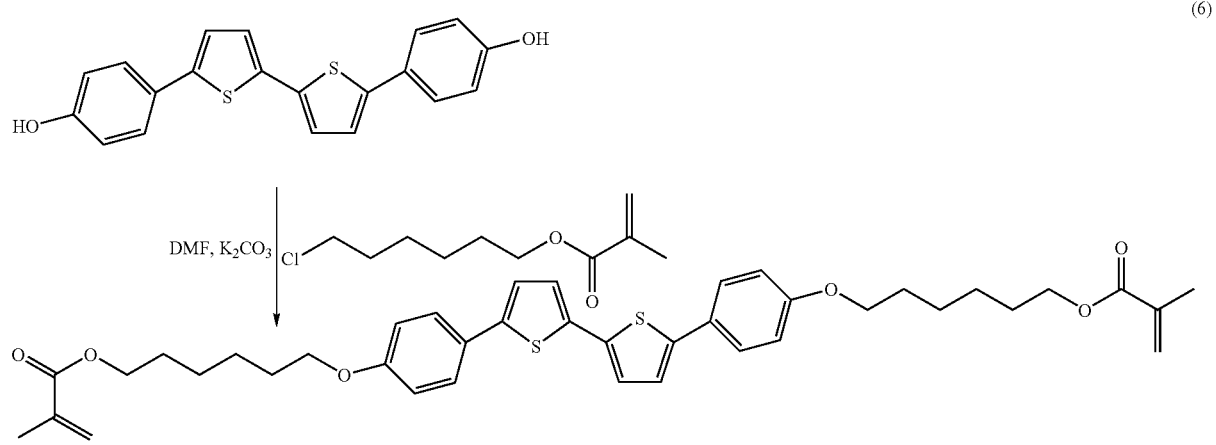

(6)

Step 6.1: 2-Methyl-acrylic acid 6-[4-(5'-{4-[6-(2-methyl-acyloxyy-hexyloxy]-phenyl}-[2,2]bithiophenyl-5-yl)-phenoxy]-hexyl ester 2,5'-Bis(4-hydroxyphenyl)bithiophene (0.50 g, 1.43 mol), potassium carbonate (0.59 g, 4.29 mmol), 6-chlorohexyl methacrylate (0.88 g, 4.29 mmol) and potassium iodide (0.71 g, 4.29 mmol) are dissolved in DMF (70 ml). This mixture is stirred overnight at 70° C. under nitrogen. After cooling, water (100 ml) is added, followed by extraction with ethyl acetate (3×70 ml). The organic phases are combined, dried and evaporated under reduced pressure. Column chromatography on silica, eluting with petrol/ethyl acetate (9:1 to 7:3), to give a yellow solid, which is recrystallised from ethyl acetate to give yellow crystals (0.43 g, 44%). $^1$H NMR (300 MHz, CDCl$_3$): δ (ppm) 7.51 (d, J (H,H)=8.8 Hz, 4H, Ar—H), 7.11 (m, 4H, Ar—H), 6.90 (d, J (H,H)=8.8 Hz, 4H, Ar—H), 6.10 (m, 2H, =CH), 5.55 (m, 2H, =CH), 4.17 (t, J (H,H)=6.6 Hz, 4H, OCH$_2$), 3.99 (t, J (H,H)=6.4 Hz, OCH$_2$), 1.95 (s, 6H, CH$_3$), 1.68-1.84 (m, 8H, CH$_2$), 1.44-1.57 (m, 8H, CH$_2$); $^{13}$C NMR (75 MHz, CDCl$_3$): 167.55 (C=O), 158.80 (quat.), 142.96 (quat.), 136.51 (quat.), 135.84 (quat.), 126.88 (CH), 126.83 (quat.), 125.25 (CH), 124.19 (CH), 122.65 (CH), 114.91 (CH), 67.92 (OCH$_2$), 64.66 (OCH$_2$), 29.16 (CH$_2$), 28.58 (CH$_2$), 25.83 (CH$_2$), 18.36 (CH$_2$), 15.3 (CH$_3$). m.p. (° C.) K 104 S$_{X1}$ 187 S$_X$ 204 I.

Example 7

Compound (7) is prepared as follows:

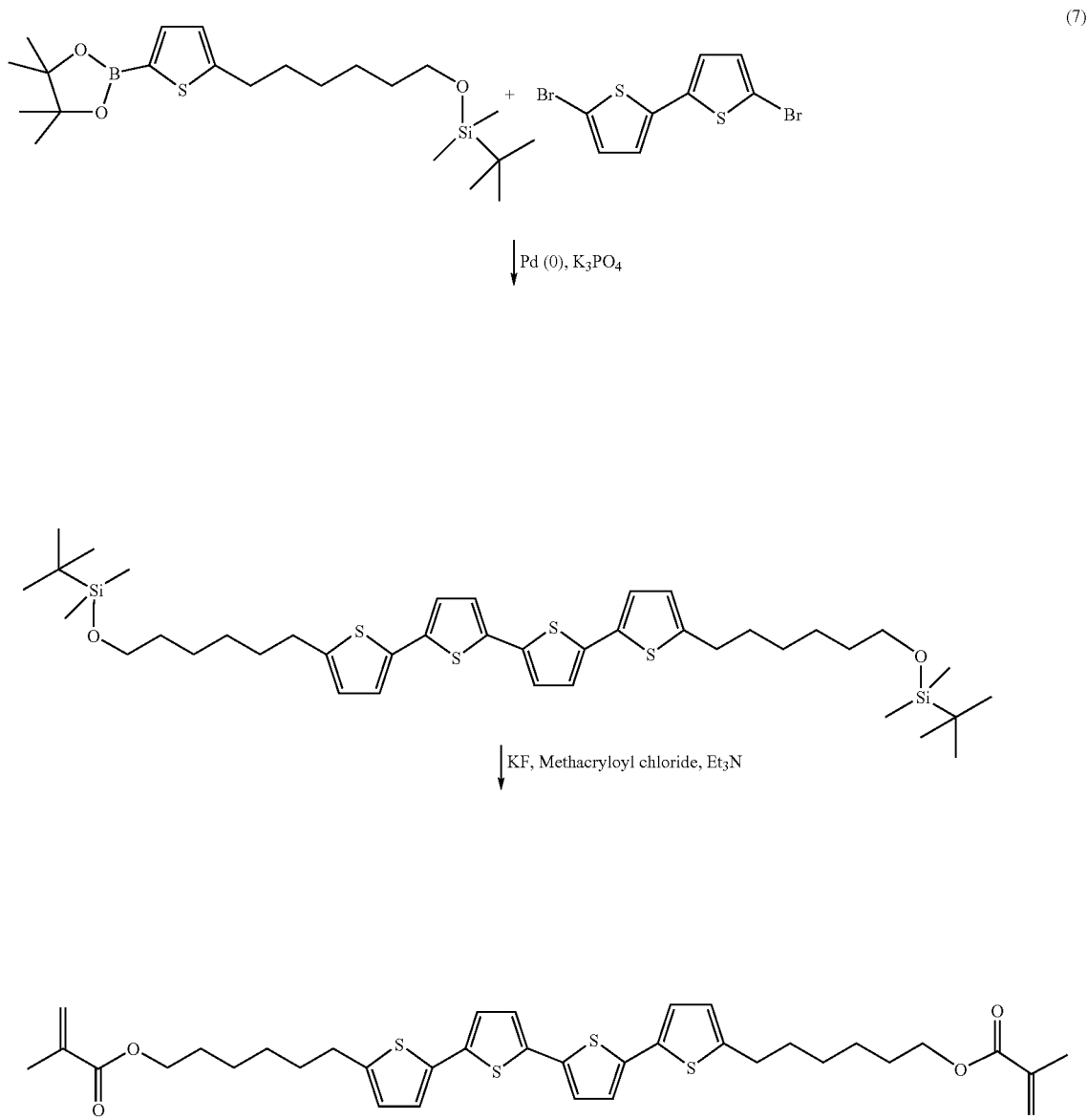

(7)

Step 7.1: 5,5'''-Bis-[6-(tert-butyl-dimethyl-silanyloxy)-hexyl]-[2,2';5',2'';5'',2''']quaterthiophene 2-[6-(Tert-butyldimethylsilanyloxy)hexyl]thiophen-5-yl pinacol boronate (0.80 g, 1.88 mmol), 5,5'-dibromo-2,2'-bithiophene (0.28 g, 0.87 mmol), tetrakis(triphenylphosphine)palladium(0) (0.03 g, 0.03 mmol), 2.5M aqueous potassium phosphate (1 mL) and THF (16 mL) are charged into a sealed tube. The reaction mixture is heated at 140° C. for 12 minutes in an Emrys Creator (Personal Chemistry Ltd) microwave reactor. The reaction mixture is poured into water (100 mL) and extracted into diethyl ether (2×100 mL). The combined extracts are washed water (100 mL), dried over sodium sulphate and concentrated in vacuo. Purification by column chromatography on reverse phase silica, eluting with (THF/acetonitrile) 2:9 to 4:6), followed by recrystallisation from cyclohexane afforded the product as an orange solid (0.87 g, 61%). $^1$H NMR (CDCl$_3$, 300 MHz): δ 7.03 (d, $^3$J=3.6 Hz, 2H), 6.99 (d, $^3$J=3.6 Hz, 2H), 6.98 (d, $^3$J=3.6 Hz, 2H), 6.68 (d, $^3$J=3.6 Hz, 2H), 3.61 (t, $^3$J=6.5 Hz, 4H), 2.79 (t, $^3$J=7.5 Hz, 4H), 1.69 (m, 4H), 1.53 (m, 4H), 1.40 (m, 8H), 0.90 (s, 18H), 0.05 (s, 12H); $^{13}$C NMR (CDCl$_3$, 75 MHz): 6145.5, 136.7, 135.4, 134.5, 124.9, 124.0, 123.6, 123.4, 63.2, 32.7, 31.6, 30.1, 28.9, 26.0, 25.6, 18.4, 5.2.

Step 7.2: 2-Methacrylic acid 6-{5'''-[5-(2-methylacryloyloxy)hexyl]-[2,2',5',2'';5'',-2''']quaterthiophen-5-yl}hexyl ester To a stirred solution of 5,5'''-bis-[6-(tert-butyldimethylsilanyloxy)hexyl]-[2,2';5',2'';5'',2''']-quaterthiophene (0.75 g, 0.99 mmol) in dry THF (20 ml) at 40° C. is added a solution of tetrabutyl ammonium fluoride (4 ml of a 1M solution in THF, 4 mmol) and the resulting solution is stirred for 2 h. The reaction is poured into water (50 ml), stirred for 20 min and filtered. The precipitate is washed with water (3×50 ml) and acetone (3×50 ml) and dried under vacuum. The resulting crude product is dissolved in NMP (50 ml) by sonication for 30 min at 40° C. The resulting red solution is filtered, and thentriethylamine (1 mL) and methacryloyl chloride (0.8 g, 7.6 mmol) are added and the reaction stirred for 4 h. The reaction mixture is poured into water (100 mL) and the resulting precipitate filtered. Purification by column chromatography on silica, eluting with dichloromethane afforded the product as an orange solid after recrystallisation from diethyl ether (250 mg, 40%). $^1$H NMR (CDCl$_3$, 300 MHz): δ 7.03 (d, $^3$J=3.6 Hz, 2H), 6.99 (d, $^3$J=3.6 Hz, 2H), 6.98 (d, $^3$J=3.6 Hz, 2H), 6.68 (d, $^3$J=3.6 Hz, 2H), 6.09 (br s, 2H, =CH), 5.54 (br s, 2H, =CH), 4.15 (t, $^3$J=6.5 Hz, 4H), 2.80 (t, $^3$J=7.1 Hz, 4H), 1.94 (s, 6H), 1.68 (m, 8H), 1.43 (m, 8H); $^{13}$C NMR (CDCl$_3$, 75 MHz): δ 167.9 (C=O), 145.5, 136.9, 136.7, 135.4, 134.5, 127.3, 125.6, 124.9, 124.0, 123.6, 123.4, 65.1, 32.7, 31.6, 30.1, 28.9, 26.0, 25.6. HRMS 666.1978 (calc. for C$_{36}$H$_{42}$O$_4$S$_4$ 666.1966). Anal. Calcd for C$_{36}$H$_{42}$O$_4$S$_4$: C, 64.8; H, 6.35. Found: C, 65.1; H, 6.6. m.p. (° C.) K 50 S$_X$ 125 I.

Example 8

Compound (8) is prepared as follows:

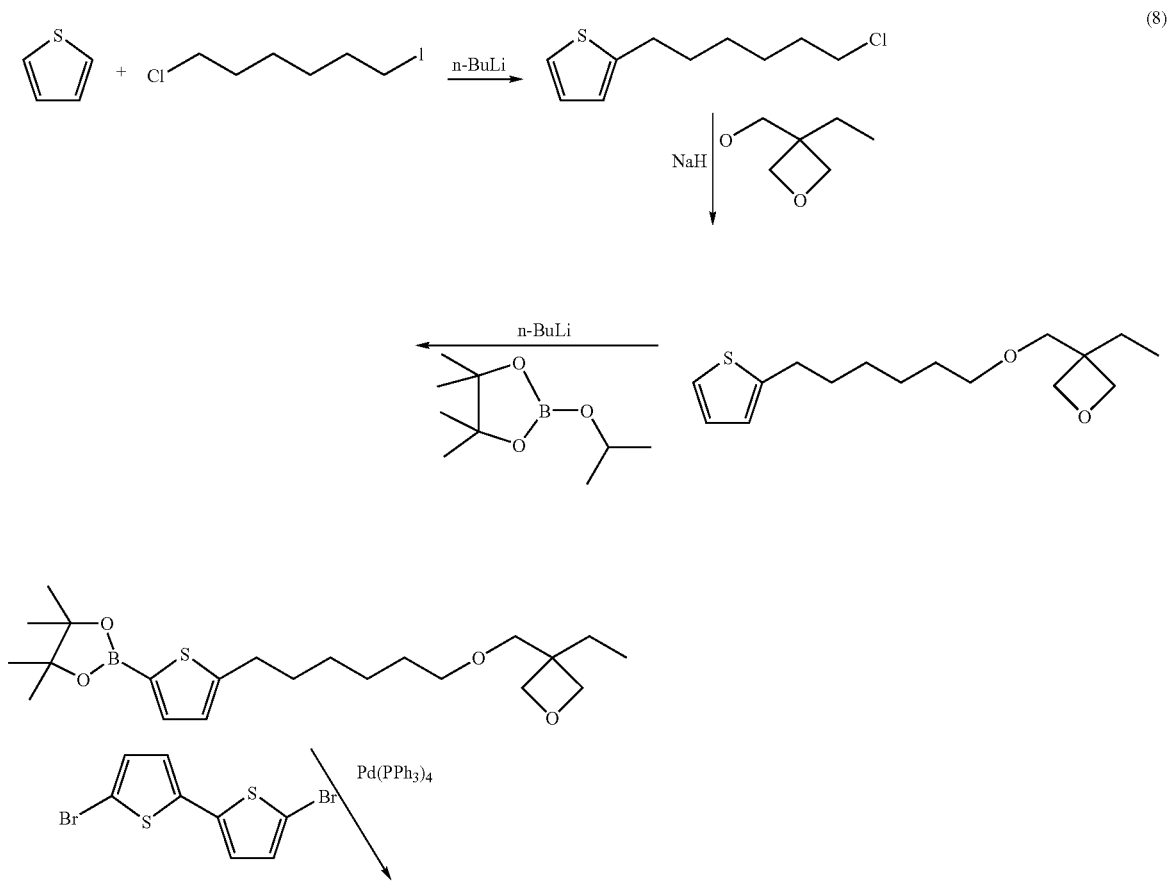

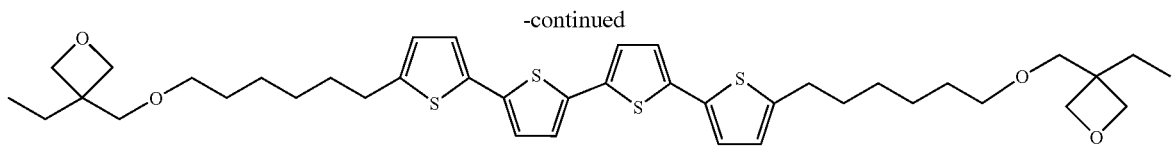

Step 8.1: 2-(6-Chlorohexyl)thiophene

To a stirred solution of thiophene (5.0 g, 59.5 mmol) in dry THF (50 ml) is added n-butyllithium (2.5 M in hexanes, 20.0 ml, 50.0 mmol) dropwise at −78° C. under nitrogen. After complete addition, the mixture is allowed to warm to room temperature, with stirring, over 2 h, followed by the addition of 1-chloro-6-iodohexane (12.3 g, 50.0 mmol). The resultant mixture is stirred overnight at room temperature. The reaction is quenched with sat. aq. ammonium chloride, and the reaction mixture is extracted with ethyl acetate (3×70 ml). The combined organic extracts are washed with water, brine, and dried over magnesium sulphate. The solvent is removed under reduced pressure and the residue is chromatographed (silica gel, petroleum ether), to give a pale yellow oil (9.3 g, 92%). $^1$H NMR (300 MHz, CDCl$_3$): δ (ppm) 7.06 (dd, J=5.1 Hz, 1.2 Hz, 1H, Ar—H), 6.87 (dd, J=5.1 Hz, 3.4 Hz, 1H, Ar—H), 6.75 (m, 1H, Ar—H), 3.48 (t, J=6.6 Hz, 2H, ClCH$_2$), 2.80 (t, J=7.4 Hz 2H, ArCH$_2$), 1.61-1.78 (m, 4H, CH$_2$), 1.29-1.50 (m, 4H, CH$_2$); $^{13}$C NMR (75 MHz, CDCl$_3$): δ (ppm) 145.5 (quat.), 126.7 (CH), 124.1 (CH), 122.9 (CH), 45.1 (CH$_2$), 32.6 (CH$_2$), 31.7 (CH$_2$), 29.9 (CH$_2$), 28.4 (CH$_2$) 26.7 (CH$_2$); MS (m/e) 204 (M$^+$, 9%), 202 (M$^+$, 3%), 97 (100).

Step 8.2: 3-Ethyl-3-(6-thiophen-2-yl-hexyloxymethyl)-oxetane

3-Ethyl-3-oxtanemethanol (10.0 g, 86.0 mmol) is added slowly to a suspension of sodium hydride (60% dispersion in mineral oil, 3.44 g, 86.0 mmol) in DMF (150 ml) at 0° C., with stirring, under nitrogen. After complete addition, the ice-bath is removed and the mixture is stirred another 20 min, followed by the addition of 2-(6-chlorohexyl)thophene (16.22 g, 80.0 mmol). The resultant mixture is stirred overnight, then water (200 ml) is added and the mixture extracted with ethyl acetate (3×100 ml). The combined extracts are washed with water and brine, then dried (Na$_2$SO$_4$) and evaporated under reduced pressure. The residue is purified by column chromatography, eluting with petroleum ether/ethyl acetate (100:0 to 9:1), to give a pale brown oil (13.74 g, 61%). $^1$H NMR (300 MHz, CDCl$_3$): δ (ppm) 7.07 (dd, J=5.1 Hz, 1.1 Hz, 1H, Ar—H), 6.88 (dd, J=5.0 Hz, 1.1 Hz, 1H, Ar—H), 6.76 (m, 1H, Ar—H), 4.43 (d, J=5.8 Hz, 2H, OCH$_2$), 4.36 (d, J=5.8 Hz, 2H, OCH$_2$), 3.50 (s, 2H, OCH$_2$), 3.43 (t, J=6.4 Hz, 2H, OCH$_2$), 2.81 (t, J=7.6 Hz 2H, ArCH$_2$), 1.37-1.77 (m, 10H, CH$_2$), 0.87 (t, J=7.6 Hz, 6H, CH$_3$); $^{13}$C NMR (75 MHz, CDCl$_3$): δ (ppm) 145.6 (quat.), 126.6 (CH), 123.9 (CH), 122.7 (CH), 78.5 (OCH$_2$), 73.4 (OCH$_2$), 71.5 (OCH$_2$), 43.4 (quat.), 31.8 (CH$_2$), 29.8 (CH$_2$), 29.5 (CH$_2$), 28.9 (CH$_2$), 26.8 (CH$_2$) 25.9 (CH$_2$), 8.2 (CH$_3$); MS (m/e): 282 (M$^+$, 2%), 166 (8), 123 (39), 110 (22), 97 (100).

Step 8.3: 2-{5-[6-(3-Ethyl-oxetan-3-ylmethoxy)-hexyl]thiophen-2-yl}-4,4,5,5-tetramethyl-[1,3,2]dioxaborolane To a stirred solution of 3-ethyl-3-(6-thiophen-2-yl-hexyloxymethyl)-oxetane (6.0 g, 21.28 mmol) in dry THF (70 ml) is added n-butyllithium (2.5 M in hexanes, 8.10 ml, 21.28 mmol) dropwise at −78° C. under nitrogen. After complete addition, the mixture is allowed to warm to room temperature, with stirring, over 2 h, followed by the addition of 2-isopropoxy-4,4,5,5-tetramethyl-1,3,2-dioxaborolane (3.96 g, 21.28 mmol). The resultant mixture is stirred overnight at room temperature. The reaction is quenched with water, and the reaction mixture is extracted with ethyl acetate (3×70 ml). The combined organic extracts are washed with water, brine, and dried over sodium sulphate. The solvent is removed under reduced pressure and the residue is purified by column chromatography on silica, eluting with petroleum ether/ethyl acetate (9:1), to give a yellow oil (6.28 g, 72%). $^1$H NMR (300 MHz, CDCl$_3$): δ (ppm) 7.45 (d, J=3.4 Hz, 1H, Ar—H), 6.85 (d, J=3.4 Hz, 1H, Ar—H), 4.44 (d, J=5.8 Hz, 2H, OCH$_2$), 4.36 (d, J=5.8 Hz, 2H, OCH$_2$), 3.51 (s, 2H, OCH$_2$), 3.45 (t, J=6.4 Hz, 2H, OCH$_2$), 2.83 (t, J=7.6 Hz 2H, ArCH$_2$), 1.32-1.77 (m, 22H, CH$_2$ and CH$_3$), 0.88 (t, J=7.4 Hz, 3H, CH$_3$); δ (ppm) 153.5 (quat.), 145.6 (quat.), 137.3 (CH), 125.9 (CH), 83.9 (quat.), 78.6 (OCH$_2$), 73.4 (OCH$_2$), 71.5 (OCH$_2$), 43.4 (quat.), 31.6 (CH$_2$), 30.1 (CH$_2$), 29.4 (CH$_2$), 28.8 (CH$_2$), 26.8 (CH$_2$), 25.9 (CH$_2$), 24.8 (CH$_3$), 8.2 (CH$_3$); MS (m/e): 408 (M$^+$, 0.5%), 223 (27), 165 (30), 141 (35), 123 (100), 97 (52).

Step 8.4

Tetrakis(triphenylphosphine)palladium(0) (0.10 g) is added to a solution of 5,5'-dibromo-2,2'-thiophene (0.50 g, 1.54 mmol) in dry THF (70 ml), with stirring, under nitrogen. After 20 min, 2-{5-[6-(3-ethyl-oxetan-3-ylmethoxy)-hexyl]thiophen-2-yl}-4,4,5,5-tetramethyl-[1,3,2]dioxaborolane (1.51 g, 3.70 mmol) and a solution of potassium carbonate (1.02 g, 7.40 mmol) in water (10 ml) is added. The resultant mixture is heated at reflux for 2 h. After cooling, water (50 ml) is added and the reaction mixture extracted with ethyl acetate (3×70 ml) and the combined extracts dried over sodium sulphate. The solvent is removed under reduced pressure and the residue washed with diethyl ether in Buchner funnel to give a yellow solid, which is recrystallised with toluene to offer yellow crystals (0.58 g, 52%). $^1$H NMR (300 MHz, CDCl$_3$): δ (ppm) 6.96-7.03 (m, 6H, Ar—H), 6.68 (d, J=3.5 Hz, 2H, Ar—H), 4.45 (d, J=5.7 Hz, 4H, OCH$_2$), 4.38 (d, J=5.7 Hz, 4H, OCH$_2$), 3.52 (s, 4H, OCH$_2$), 3.45 (t, J=6.4 Hz, 4H, OCH$_2$), 2.79 (t, J=7.6 Hz 4H, ArCH$_2$), 1.37-1.78 (m, 20H, CH$_2$), 0.88 (t, J=7.6 Hz, 6H, CH$_3$); $^{13}$C NMR (75 MHz, CDCl$_3$): δ (ppm) 145.4 (quat.), 136.7 (quat.), 135.4 (quat.), 134.5 (quat.), 124.9 (CH), 124.0 (CH), 123.6 (CH), 123.4 (CH), 78.6 (OCH$_2$), 73.4 (OCH$_2$), 71.5 (OCH$_2$), 43.4 (quat.), 31.6 (CH$_2$), 30.2 (CH$_2$), 29.5 (CH$_2$), 28.9 (CH$_2$), 26.8 (CH$_2$) 25.9 (CH$_2$), 8.3 (CH$_3$). m.p. (° C.) K 82 S$_X$ 110 I

Example 9

Compound (9) is prepared as follows:

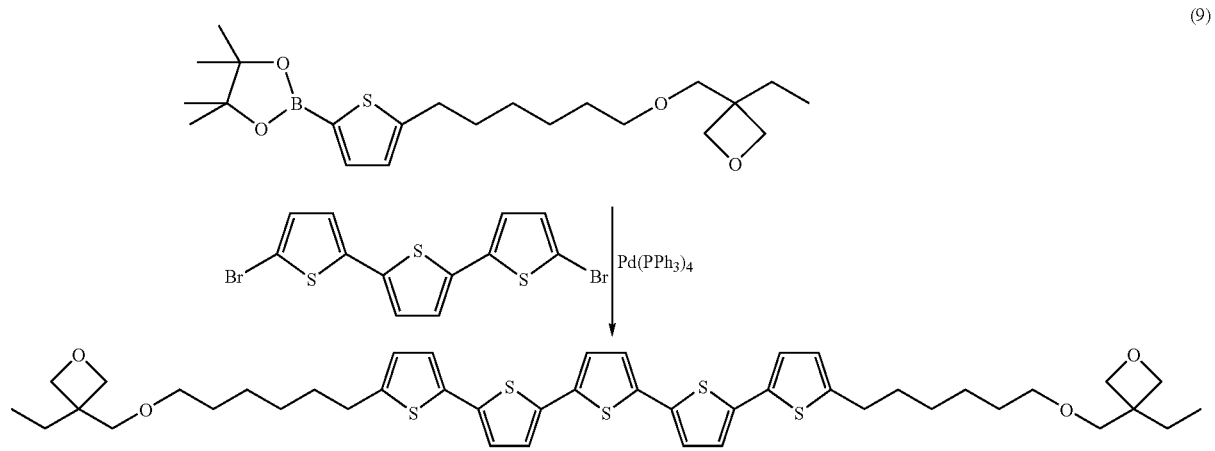

Step 9.1

Tetrakis(triphenylphosphine)palladium(0) (0.05 g) is added to a solution of 5',5''-dibromo-[2,2';5',2'']terthiophene (0.10 g, 0.25 mmol) in dry THF (30 ml), with stirring, under nitrogen. After 20 min, 2-{5-[6-(3-Ethyl-oxetan-3-yl-methoxy)-hexyl]thiophen-2-yl}-4,4,5,5-tetramethyl-[1,3,2]dioxaborolane (0.25 g, 0.60 mmol) and a solution of potassium carbonate (0.17 g, 1.23 mmol) in water (5 ml) is added. The resultant mixture is heated at reflux for 1.5 h. After cooling, water (100 ml) is added and the precipitate filtered off, washed with water and diethyl ether, to give a red solid, which is recrystallised with toluene to offer red crystals (0.14 g, 70%). $^1$H NMR (300 MHz, CDCl$_3$): δ (ppm) 6.97-7.07 (m, 8H, Ar—H), 6.68 (d, J=2.5 Hz, 2H, Ar—H), 4.45 (d, J=5.7 Hz, 4H, OCH$_2$), 4.38 (d, J=5.7 Hz, 4H, OCH$_2$), 3.52 (s, 4H, OCH$_2$), 3.45 (t, J=6.4 Hz, 4H, OCH$_2$), 2.80 (t, J=7.4 Hz 4H, ArCH$_2$), 1.35-1.78 (m, 20H, CH$_2$), 0.88 (t, J=7.4 Hz, 6H, CH$_3$); $^{13}$C NMR (75 MHz, CDCl$_3$): δ (ppm) 145.5 (quat.), 136.9 (quat.), 136.0 (quat.), 135.2 (quat.), 134.5 (quat.), 125.0 (CH), 124.2 (CH), 124.1 (CH), 123.6 (CH), 123.5 (CH), 78.7 (OCH$_2$), 73.4 (OCH$_2$), 71.5 (OCH$_2$), 43.4 (quat.), 31.5 (CH$_2$), 30.2 (CH$_2$), 29.5 (CH$_2$), 28.9 (CH$_2$), 26.8 (CH$_2$) 25.9 (CH$_2$), 8.3 (CH$_3$). m.p. (° C.) K 98 S$_X$ 180 I

Example 10

Compound (10) is prepared as follows:

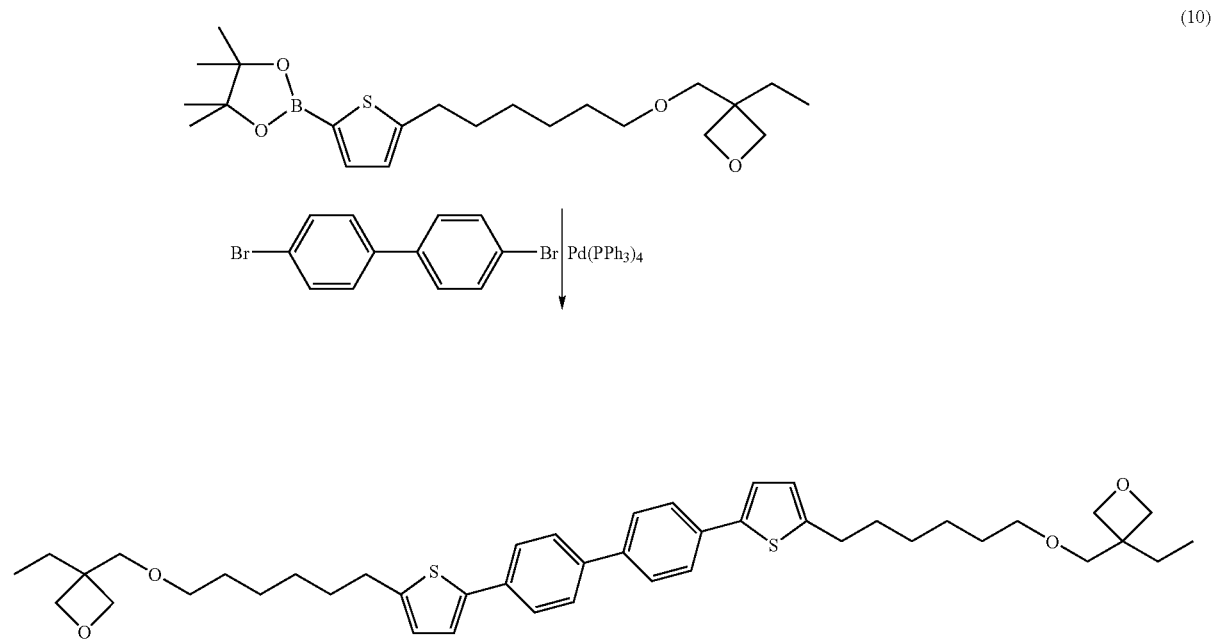

Step 10.1

Tetrakis(triphenylphosphine)palladium(0) (0.01 g) is added to a solution of 4,4'-dibromobitphenyl (0.12 g, 0.38 mmol) in dry THF (30 ml), with stirring, under nitrogen. After 20 min, 2-{5'-[6-(3-ethyloxyoxetan-3-ylmethoxy)hexyl]thioen-2-yl}-4,4,5,5-tetramethyl-[1,3,2]dioxaborolane (0.50 g, 1.22 mmol) and a solution of potassium carbonate (0.35 g, 2.5 mmol) in water (5 ml) is added. The resultant mixture is heated at reflux for 1.5 h. After cooling, water (50 ml) is added. The precipitate is filtered and washed with diethyl ether, to give a yellow solid, which is recrystallised with toluene to offer yellow crystals (0.18 g, 65%). $^1$H NMR (300 MHz, CDCl$_3$): δ (ppm) 7.61 (m, 8H, Ar—H), 7.17 (d, J=3.6 Hz, 2H, Ar—H), 6.76 (d, J=3.6 Hz, 2H, Ar—H), 4.45 (d, J=5.8 Hz, 4H, OCH$_2$), 4.38 (d, J=5.8 Hz, 4H, OCH$_2$), 3.52 (s, 4H, OCH$_2$), 3.45 (t, J=6.4 Hz, 4H, OCH$_2$), 2.83 (t, J=7.6 Hz 4H, ArCH$_2$), 1.40-1.78 (m, 20H, CH$_2$), 0.88 (t, J=7.5 Hz, 6H, CH$_3$); $^{13}$C NMR (75 MHz, CDCl$_3$): δ (ppm) 145.7 (quat.), 141.3 (quat.), 139.0 (quat.), 133.8 (quat.), 127.1 (CH), 125.8 (CH), 125.2 (CH), 122.8 (CH), 78.7 (OCH$_2$), 73.4 (OCH$_2$), 71.6 (OCH$_2$), 43.4 (quat.), 31.6 (CH$_2$), 30.3 (CH$_2$), 29.5 (CH$_2$), 28.9 (CH$_2$), 26.8 (CH$_2$) 25.9 (CH$_2$), 8.3 (CH$_3$). m.p. (° C.) K 94 S$_{X1}$ 168 S$_X$ 171 I.

Example 11

Compound (11) is prepared as follows:

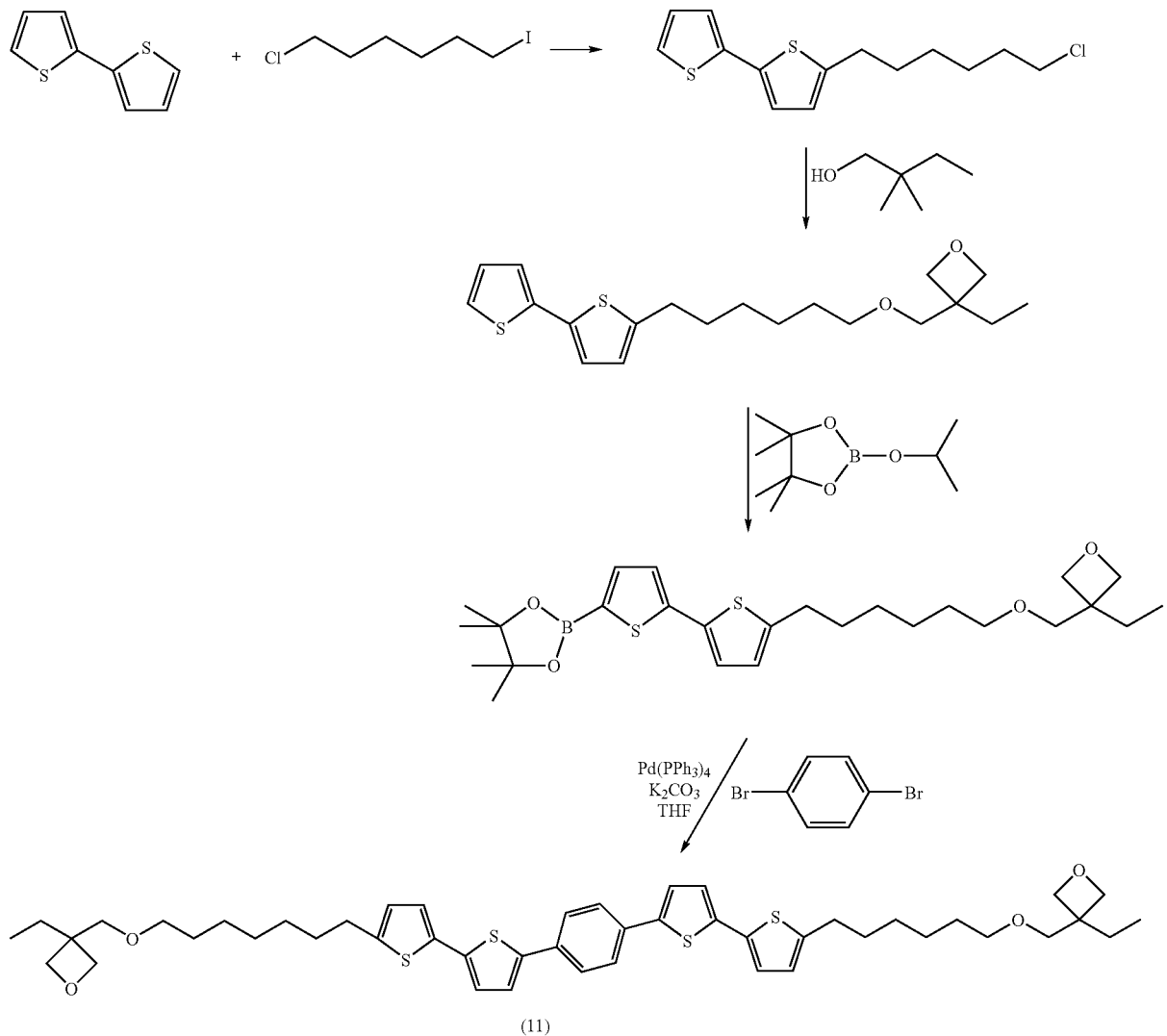

(11)

Step 11.1: 5-(6-chlorohexyl)-2,2'-bithiophene

To a stirred solution of 2,2'-bithiophene (10.0 g, 60.24 mmol) in anhydrous THF (150 ml) is added n-butyllithium (2.5 M in hexanes, 20.0 ml, 50.0 mmol) dropwise at −78° C. under nitrogen. After complete addition, the mixture is allowed to warm to room temperature, with stirring, over 2 h, followed by the addition of 1-chloro-6-iodohexane (14.55 g, 50.0 mmol). The resultant mixture is stirred overnight at room temperature. The reaction is quenched with sat. aq. NH$_4$Cl, and the reaction mixture is extracted with ethyl acetate (3×100 ml). The combined organic extracts are washed with water, brine, and dried over sodium sulphate. The solvent is removed under reduced pressure and the residue is purified by column chromatography on silica, eluting with petroleum ether, to give 5-(6-chlorohexyl)-2,2'-bithiophene as a white solid (7.73 g, 54%). $^1$H NMR (300 MHz, CDCl$_3$): δ (ppm) 7.14 (d, J=5.3 Hz, 1.3 Hz, 1H, Ar—H), 7.08 (dd, J=3.5 Hz, 1.1 Hz, 1H, Ar—H), 6.97 (m, 2H, Ar—H), 6.66 (d, J=3.5 Hz, 1H, Ar—H), 3.51 (d, J=6.6 Hz, 2H, ClCH$_2$), 2.78 (t, J=7.1 Hz 2H, ArCH$_2$), 1.61-1.81 (m, 4H, CH$_2$), 1.35-1.51 (m, 4H, CH$_2$); MS (m/e): 282 (M$^+$, 2%), 166 (8), 123 (39), 110 (22), 97 (100).

Step 11.2: 3-(6-[2,2']bithiophenyl-5-yl-hexyloxymethyl)-3-ethyl-oxetane

3-Ethyl-3-oxtanemethanol (3.10 g, 26.72 mmol) is added slowly to a suspension of sodium hydride (60% dispersion in mineral oil, 1.07 g, 26.72 mmol) in DMF (70 ml) at 0° C., with stirring, under nitrogen. After complete addition, the ice-bath is removed and the mixture is stirred another 20 min, followed by the addition of 5-(6-chlorohexyl)-2,2'-bithiophene (7.61 g, 26.72 mmol). The resultant mixture is stirred overnight, then water (100 ml) is added and the mixture extracted with ethyl acetate (3×70 ml). The combined extracts are washed with water and brine, then dried (Na$_2$SO$_4$) and evaporated under reduced pressure. The residue is purified by column chromatography, eluting with petroleum ether/ethyl acetate (100:0 to 9:1), to give 3-(6-[2,2']bithiophenyl-5-yl-hexyloxymethyl)-3-ethyl-oxetane as a brown oil (6.34 g, 65%). $^1$H NMR (300 MHz, CDCl$_3$): δ (ppm) 7.15 (dd, J=5.0 Hz, 1.1 Hz, 1H, Ar—H), 7.05 (dd, J=3.6 Hz, 1.1 Hz, 1H, Ar—H), 6.92 (m, 2H, Ar—H), 6.62 (d, J=3.4 Hz, 1H, Ar—H), 4.40 (d, J=5.9 Hz, 2H, OCH$_2$), 4.32 (d, J=5.9 Hz, 2H, OCH$_2$), 3.45 (s, 2H, OCH$_2$), 3.38 (t, J=6.4 Hz, 2H, OCH$_2$), 2.73 (t, J=7.6 Hz 2H, ArCH$_2$), 1.32-1.73 (m, 10H, CH$_2$), 0.84 (t, J=7.5 Hz, 6H, CH$_3$); $^{13}$C NMR (75 MHz, CDCl$_3$): δ (ppm) 144.9 (quat.), 137.9 (quat.), 134.8 (quat.), 127.7 (CH), 124.8 (CH), 123.6 (CH), 123.3 (CH), 122.9 (CH), 78.4 (OCH$_2$), 73.4 (OCH$_2$), 71.4 (OCH$_2$), 43.4 (quat.), 31.6 (CH$_2$), 30.1 (CH$_2$), 29.5 (CH$_2$), 28.9 (CH$_2$), 26.8 (CH$_2$) 26.0 (CH$_2$), 8.2 (CH$_3$). 364 (M$^+$, 13%) 205 (11), 179 (100).

Step 11.3: 2-{5'-[6-(3-ethyl-oxetan-3-ylmethoxy)hexyl]-[2,2']bithiophenyl-5-yl}-4,4,5,5-tetramethyl-[1,3,2]dioxaborolane To a stirred solution of 3-(6-[2,2']bithiophenyl-5-yl-hexyloxymethyl)-3-ethyl-oxetane (6.0 g, 16.46 mmol) in anhydrous THF (100 ml) is added n-butyllithium (2.5 M in hexanes, 7.0 ml, 17.50 mmol) dropwise at −78° C. under nitrogen. After complete addition, the mixture is allowed to warm to room temperature, with stirring, over 2 h, followed by the addition of 2-isopropoxy-4,4,5,5-tetramethyl-1,3,2-dioxaborolane (3.26 g, 17.5 mmol). The resultant mixture is stirred overnight at room temperature. The reaction is quenched with sat. aq. NH$_4$Cl, and the reaction mixture is extracted with ethyl acetate (3×100 ml). The combined organic extracts are washed with water, brine, and dried over sodium sulphate. The solvent is removed under reduced pressure and the residue is further purified by column chromatography on silica, eluting with petroleum ether/ethyl acetate (9:1 to 4:1), to give 2-{5'-[6-(3-ethyl-oxetan-3-ylmethoxy)hexyl]-[2,2']bithiophenyl-5-yl}-4,4,5,5-tetramethyl-[1,3,2] dioxaborolane as a blue oil (4.53 g, 56%). $^1$H NMR (300 MHz, CDCl$_3$): δ (ppm) 7.49 (d, J=3.6 Hz, 1H, Ar—H), 7.14 (d, J=3.6 Hz, 1H, Ar—H), 7.03 (d, J=3.6 Hz, 1H, Ar—H), 6.66 (d, J=3.6 Hz, 1H, Ar—H), 4.43 (d, J=5.8 Hz, 2H, OCH$_2$), 4.34 (d, J=5.8 Hz, 2H, OCH$_2$), 3.48 (s, 2H, OCH$_2$), 3.42 (t, J=6.6 Hz, 2H, OCH$_2$), 2.76 (t, J=7.5 Hz, 2H, ArCH$_2$), 1.32-1.75 (m, 22H, CH$_2$ and CH$_3$), 0.86 (t, J=7.5 Hz, 3H, CH$_3$); $^{13}$C NMR (75 MHz, CDCl$_3$): δ (ppm) 144.8 (quat.), 143.7 (quat.), 137.0 (CH), 133.7 (quat.), 124.0 (CH), 123.1 (CH), 123.0 (CH), 83.1 (quat.), 77.5 (OCH$_2$), 72.4 (OCH$_2$), 70.4 (OCH$_2$), 42.4 (quat.), 30.5 (CH$_2$), 29.1 (CH$_2$), 28.4 (CH$_2$), 27.8 (CH$_2$) 25.8 (CH$_2$), 24.9 (CH$_3$), 8.3 (CH$_3$); MS (m/e): 490 (M$^+$, 16%) ☐ 305 (79), 223 (25), 205 (100).

Step 11.4

Tetrakis(triphenylphosphine)palladium(0.01 g) is added to a solution of 1,4-dibromobenzene (0.12 g, 0.51 mmol) in dry THF (30 ml), with stirring, under nitrogen. After 20 min, 2-{5'-[6-(3-ethyl-oxetan-3-ylmethoxy)hexyl]-[2,2'] bithiophenyl-5-yl}-4,4,5,5-tetramethyl-[1,3,2]dioxaborolane (0.75 g, 1.53 mmol) and a solution of potassium carbonate (0.42 g, 3.04 mmol) in water (10 ml) is added. The resultant mixture is heated at reflux for 1.5 h. After cooling, water (50 ml) is added and the reaction mixture is extracted with ethyl acetate (3×50 ml) and the combined extracts dried over sodium sulphate. The solvent is removed under reduced pressure and the residue washed with diethyl ether in Buchner funnel to give a yellow solid, which is recrystallised with toluene to offer yellow crystals (0.23 g, 56%). $^1$H NMR (300 MHz, CDCl$_3$): δ (ppm) 7.58 (s, 4H, Ar—H), 7.22 (d, J=3.6 Hz, 2H, Ar—H), 7.07 (d, J=3.6 Hz, 2H, Ar—H), 7.01 (d, J=3.2 Hz, 2H, Ar—H), 6.69 (d, J=3.2 Hz, 2H, Ar—H), 4.45 (d, J=5.9 Hz, 4H, OCH$_2$), 4.38 (d, J=5.9 Hz, 4H, OCH$_2$), 3.52 (s, 4H, OCH$_2$), 3.45 (t, J=6.4 Hz, 4H, OCH$_2$), 2.80 (t, J=7.2 Hz 4H, ArCH$_2$), 1.35-1.78 (m, 20H, CH$_2$), 0.88 (t, J=7.5 Hz, 6H, CH$_3$); $^{13}$C NMR (75 MHz, CDCl$_3$): δ (ppm) 145.4 (quat.), 141.9 (quat.), 137.4 (quat.), 134.8 (quat.), 133.2 (quat.), 125.9 (CH), 124.9 (CH), 123.9 (CH), 123.7 (CH), 123.4 (CH), 78.6 (OCH$_2$), 73.5 (OCH$_2$), 71.5 (OCH$_2$), 43.5 (quat.), 31.5 (CH$_2$), 30.1 (CH$_2$), 29.5 (CH$_2$), 28.9 (CH$_2$) 26.8 (CH$_2$), 25.9 (CH$_2$), 8.2 (CH$_3$). m.p. (° C.) K 164 S$_{X1}$ 169 S$_X$ 189 I.

Example 12

Compound (12) is prepared as follows:

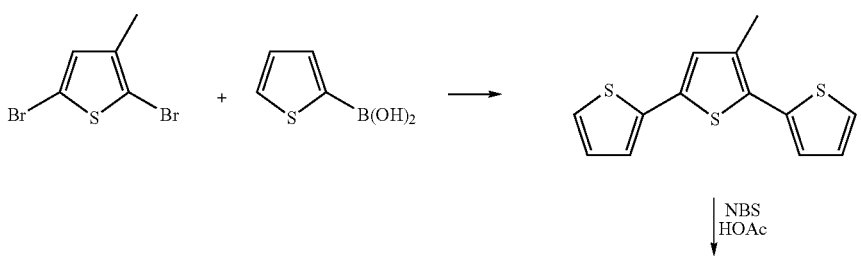

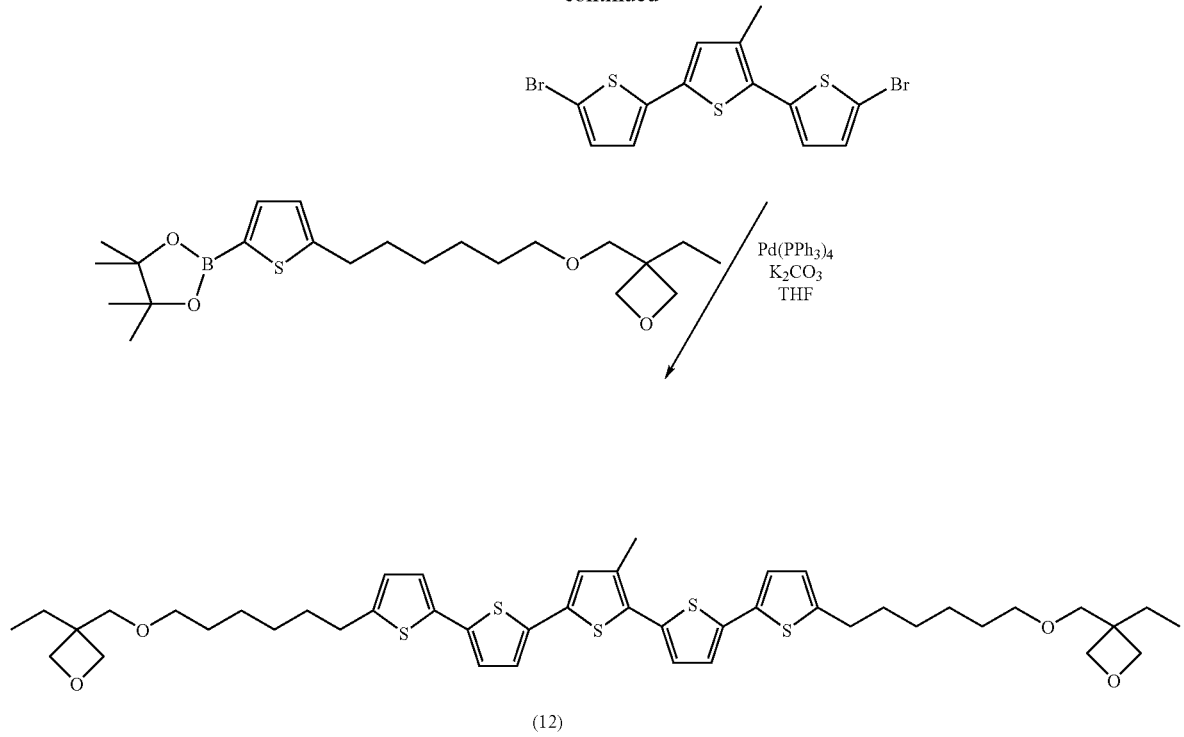

(12)

Step 12.1: 3'-Methyl-[2.2',5',2"]terthiophene

To a stirred solution of Pd$_2$(dba)$_3$ (0.30 g, 0.33 mmol) in anhydrous THF (70 ml) is added [(t-Bu$_3$)PH]BF$_4$ (0.38 g, 1.32 mmol) under N$_2$, with stirring. After 5 min, 2,5-dibromo-3-methylthiophene (7.0 g, 27.35 mmol) is introduced and this mixture is stirred for another 10 min, followed by the addition of thiophene-2-boronic acid (8.40 g, 65.65 mmol) and a solution of potassium phosphate (15 g) in water (20 ml). This mixture is heated at reflux for 3 h. After cooling, water is added and the mixture is extracted with ethyl acetate (3×70 ml), dried (Na$_2$SO$_4$) and evaporated under reduced pressure. The residue is purified by column chromatography, eluting with petroleum ether, to give a brown oil (6.05 g, 84%). $^1$H NMR (300 MHz, CDCl3): δ (ppm) 7.23 (dd, J=5.2, 1.2 Hz, 1H, Ar—H), 7.14 (dd, J=5.1, 1.2 Hz, 1H, Ar—H), 7.11 (m, 2H, Ar—H), 7.01 (m, 1H, Ar—H), 6.94 (m, 2H, Ar—H), 2.32 (s, 3H, CH$_3$); $^{13}$C NMR (75 MHz, CDCl$_3$): δ (ppm) 137.2, 136.4, 134.7, 134.6, 130.1, 128.0, 127.98, 127.6, 125.5, 125.2, 124.4, 123.7, 15.6.

Step 12.2: 5,5"-Dibromo-3'-methyl-[2,2',5',2"]terthiophene

A mixture of 3'-methyl-[2,2',5',2"]terthiophene (2.20 g, 8.38 mmol) and N-bromosuccinimide (2.99 g, 16.80 mmol) in acetic acid (30 ml) is stirred in the dark for 1 h. The precipitate formed is filtered and washed with water, then recrystallised with toluene, to give pale yellow crystals (2.28 g, 65%). $^1$H NMR (300 MHz, CDCl3): δ (ppm) 7.01 (d, J=4.0 Hz, 1H, Ar—H), 6.95 (d, J=3.7 Hz, 1H, Ar—H), 6.87 (m, 3H, Ar—H), 2.31 (s, 3H, CH$_3$); $^{13}$C NMR (75 MHz, CDCl$_3$): δ (ppm) 138.3, 137.5, 135.1, 134.1, 130.7, 130.3, 129.5, 128.0, 125.7, 123.8, 112.0, 111.2, 15.4.

Step 12.3

To a stirred solution of 5,5"-dibromo-3'-methyl-[2,2',5',2"]terthiophene (0.13 g, 0.31 mmol) in anhydrous THF (20 ml) is added tetrakis(triphenylphosphine)palladium(0) (0.05 g) under nitrogen, with stirring. After 15 min, 2-{5-[6-(3-ethyl-oxetan-3-ylmethoxy)-hexyl]thiophen-2-yl}-4,4,5,5-tetramethyl-[1,3,2]dioxaborolane (0.38 g, 0.93 mmol) and a solution of potassium carbonate (0.50 g, 3.62 mmol) in water (5 ml) is added. This mixture is heated at reflux for 1.5 h. After cooling, water is added and the mixture is extracted with ethyl acetate (3×50 ml). The extracts are dried (Na$_2$SO$_4$) and evaporated under reduced pressure. The residue is dissolved in ether (2 ml) and cooled to 0° C. The resulting crystals are filtered and washed with a little ether, to give an orange product (0.16 g, 64%). $^1$H NMR (300 MHz, CDCl$_3$): δ (ppm) 6.95-7.05 (m, 7H, Ar—H), 6.69 (m, 2H, Ar—H), 4.45 (d, J=5.9 Hz, 4H, OCH$_2$), 4.38 (d, J=5.9 Hz, 4H, OCH$_2$), 3.52 (s, 4H, OCH$_2$), 3.45 (t, J=6.4 Hz, 4H, OCH$_2$), 2.80 (t, J=7.2 Hz, 4H, ArCH$_2$), 2.40 (s, 3H, Ar—CH$_3$), 1.67-1.78 (m, 8H, CH$_2$), 1.59 (m, 4H, CH$_2$), 1.40 (m, 8H, CH$_2$), 0.88 (t, J=7.5 Hz, 6H, CH$_3$); $^{13}$C NMR (75 MHz, CDCl$_3$): δ (ppm) 145.5, 145.4, 137.5, 136.8, 135.2, 134.6, 134.52, 134.49, 134.4, 130.0, 127.8, 125.8, 124.9, 124.2, 123.6, 123.4, 123.3, 78.7, 73.4, 71.5, 43.4, 31.5, 30.1, 29.5, 28.9, 26.8, 25.9, 15.7, 8.3. m.p. (° C.) K 36 $S_X$ 65.4 N 70.9 I.
Example 13
Compound (13) is prepared as follows:
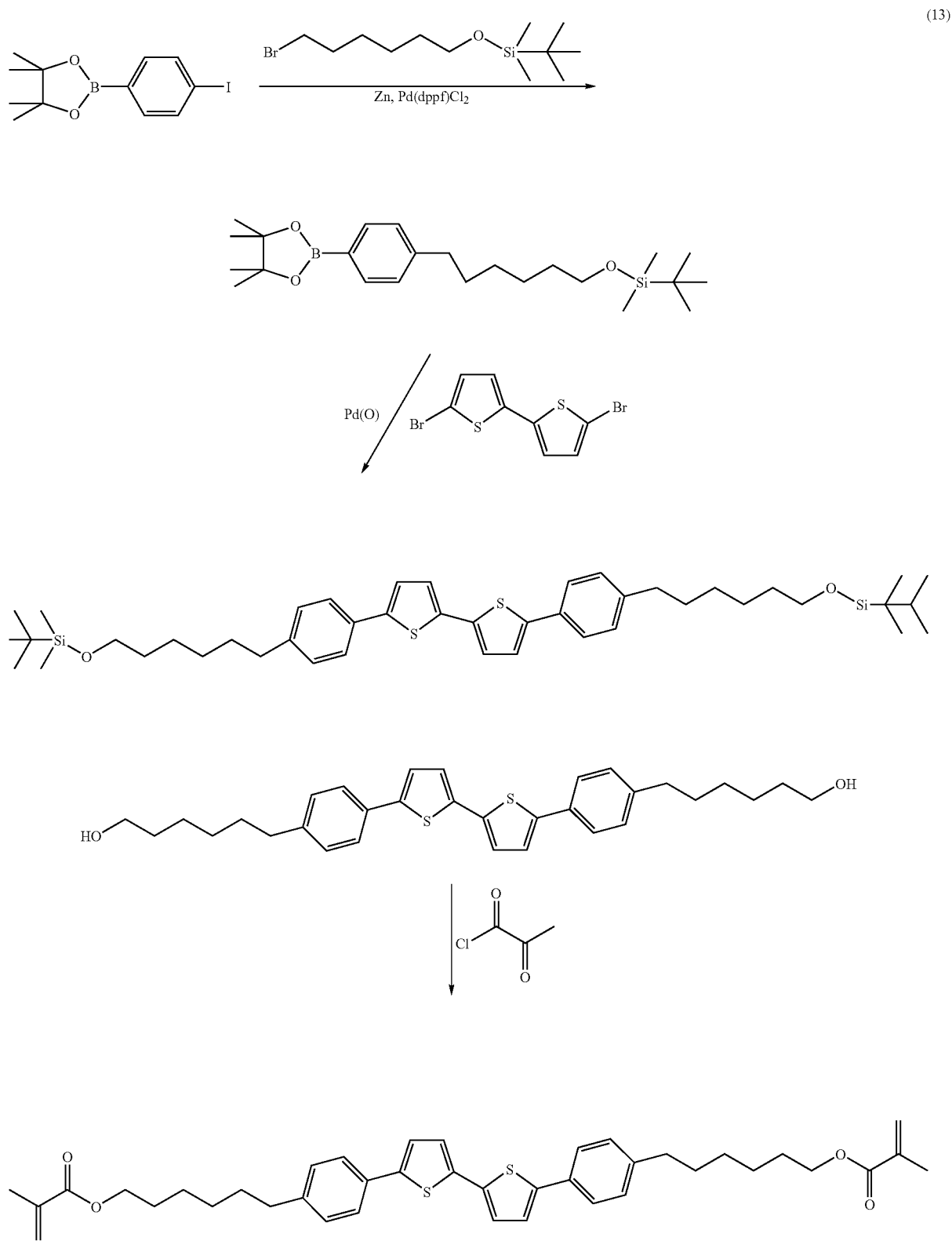

Step 13.1: 2-{4-[6-(Tert-butyl-dimethylsilanyloxy)hexyl]-phenyl}-4,4,5,5-tetramethyl-[1,3,2]dioxaborolane To a suspension of zinc powder (5.0 g, 76.46 mmol) in anhydrous DMA (30 ml) is added iodine (0.5 g, 2 mmol). This mixture is stirred until the red color of $I_2$ disappeared (ca. 2 min), followed by the addition of (6-bromohexyloxy)-tert-butyl-dimethylsilane (15.0 g, 50.79 mmol) and the mixture is stirred at 85° C. for 4.5 h, then cooled to room temperature and excess zinc allowed to settle. In another flask charged with anhydrous THF (30 ml) is added 2-(4-iodophenyl)-4,4,5,5-tetramethyl-[1,3,2]dioxaborolane (15.0 g, 45.46 mmol) and Pd(dppf)$Cl_2$ (0.85 g, 0.10 mmol). This mixture is stirred for 10 min, then the solution of organozinc reagent is transferred by cannula into the flask. The reaction mixture is stirred overnight (~16 h) at room temperature. Sat. aq. $NH_4Cl$ solution is added and the mixture is extracted with ethyl acetate (3×70 ml). The extracts are dried ($Na_2SO_4$) and evaporated under reduced pressure. The residue is purified by column chromatography, eluting with petrol/ethyl acetate (10:0 to 4:1), to give a brown oil (13.83 g, 73%). $^1$H NMR (300 MHz, $CDCl_3$): δ(ppm) 7.70 (d, J=7.9 Hz, 2H, Ar—H), 7.14 (d, J=7.9 Hz, 2H, Ar—H), 3.54 (t, J=6.6 Hz, 2H, $OCH_2$), 2.56 (t, J=7.3 Hz, 2H, $ArCH_2$), 1.27-1.65 (m, 20H, $CH_2$ and $CH_3$), 0.85 (s, 9H, $CH_3$), 0.05 (s, 6H, $CH_3$); $^{13}$C NMR (75 MHz, $CDCl_3$): δ(ppm) 146.3 (quat.), 134.9 (CH), 127.9 (CH), 83.6 (2×quat.), 63.3 ($CH_2$), 36.2 ($CH_2$), 32.9 ($CH_2$), 31.4 ($CH_2$), 29.1 ($CH_2$), 26.1 (3×$CH_3$), 25.8 ($CH_2$), 24.9 (4×$CH_3$), 18.4 (quat.), −5.2 (2×$CH_3$).

Step 1.3.2: 5,5'-Bis-{4-[6-(tert-butyl-dimethylsilanyloxy)hexyl]-phenyl}-[2,2']bithiophene To a stirred solution of 5,5'-dibromo-[2,2']bithiophene (0.60 g, 1.85 mmol) in anhydrous THF (50 ml) is added tetrakis(triphenylphosphine)palladium(0) (0.10 g) under $N_2$, with stirring. After 20 min, 2-{4-[6-(tert-butyl-dimethylsilanyloxy)hexyl]-phenyl}-4,4,5,5-tetramethyl-[1,3,2]dioxaborolane (2.30 g, 5.50 mmol) and a solution of potassium carbonate (1.50 g) in water (10 ml) is added. This mixture is heated at reflux for 2 h. After cooling, water is added and the mixture is extracted with ethyl acetate (3×50 ml). The extracts are dried ($Na_2SO_4$) and evaporated under reduced pressure. The residue is purified by column chromatography on silica, eluting with petroleum ether/ethyl acetate (from 10:0 to 4:1), to give a yellow solid (0.87 g, 64%). $^1$H NMR (300 MHz, $CDCl_3$): δ(ppm) 7.52 (d, J=8.1 Hz, 4H, Ar—H), 7.13-7.20 (m, 8H, Ar—H), 3.60 (t, J=6.4 Hz, 4H, $OCH_2$), 2.62 (t, J=7.3 Hz, 4H, Ar—$CH_2$), 1.35-1.65 (m, 16H, $CH_2$), 0.89 (s, 18H, $CH_3$), 0.05 (s, 12H, $CH_3$); $^{13}$C NMR (75 MHz, $CDCl_3$): δ(ppm) 143.2 (2×quat.), 142.5 (2×quat.), 136.3 (2×quat.), 131.5 (2×quat.), 129.0 (4×CH), 125.5 (4×CH), 124.3 (2×CH), 123.3 (2×CH), 63.3 (2×$OCH_2$), 35.6 (2×$CH_2$), 32.8 (2×$CH_2$), 31.4 (2×$CH_2$), 29.1 (2×$CH_2$), 26.0 (3×$CH_3$), 25.7 ($CH_2$), 18.4 (2×quat.), −5.2 (2×$CH_3$). HRMS 746.4080 (calc. for $C_{44}H_{66}O_2S_2Si_2$ 746.4043).

Step 13.3: 2-Methylacrylic acid 6-[4-(5'-{4-[6-(2-methylacryloyloxy)-hexyl]phenyl}-[2,2']bithiophenyl-5-yl)phenyl]hexyl ester A mixture of 5,5'-bis-{4-[6-(tert-butyl-dimethylsilanyloxy)hexyl]-phenyl}-[2,2']bithiophene (0.70 g, 0.94 mmol) and tetrabutylammonium fluoride (1M in THF, 3.0 ml, 3.0 mmol) in THF (20 ml) is stirred for 15 h at room temperature. The precipitate is filtrated and washed with water and diethyl ether, then dried to give a yellow solid (0.30 g, 62%). This solid is dissolved in N-methyl-2-pyrrolidone (20 ml), followed by the addition of methacryloyl chloride (0.24 g, 2.30 mmol). To this solution is added triethylamine (0.25 g, 2.50 mmol) dropwise over 10 min. The reaction mixture is stirred for 16 h at room temperature, then water is added. The mixture is extracted with ethyl acetate (3×70 ml), and the combined organic phases is washed with brine and dried ($Na_2SO_4$). The solvent is removed under reduced pressure. The residue is purified by column chromatography on silica, eluting with petroleum/ethyl acetate (10:0 to 4:1), to give a yellow solid, which is recrystallised with ethyl acetate to give yellow crystals (0.21 g, 57%). $^1$H NMR (300 MHz, $CDCl_3$): δ(ppm) 7.52 (d, J=8.1 Hz, 4H, Ar—H), 7.17 (m, 8H, Ar—H), 6.09 (m, 2H, =$CH_2$), 5.55 (m, 2H, =$CH_2$), 4.14 (t, J=6.6 Hz, 4H, $OCH_2$), 2.62 (t, J=7.4 Hz, 4H, $ArCH_2$), 1.94 (s, 6H, $CH_3$), 1.65 (m, 8H, $CH_2$), 1.41 (m, 8H, $CH_2$); $^1$H NMR (300 MHz, $CDCl_3$): δ(ppm) 167.6 (2×C=O), 143.2 (2×quat.), 142.3 (2×quat.), 136.5 (2×quat.), 136.3 (2×quat.), 131.6 (2×quat.), 129.0 (4×CH), 125.6 (4×CH), 125.2 [2×(=$CH_2$)], 124.3 (2×CH), 123.3 (2×CH), 64.8 (2×$CH_2$), 35.6 (2×$CH_2$), 31.3 (2×$CH_2$), 28.9 (2×$CH_2$), 28.6 (2×$CH_2$), 25.9 (2×$CH_2$), 18.4 (2×$CH_3$).

Example (14)

Compound (14) is prepared as follows:

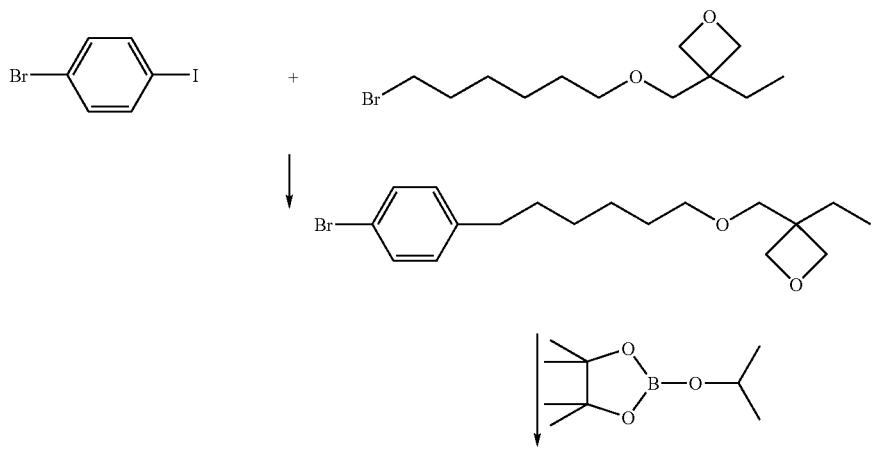

(14)

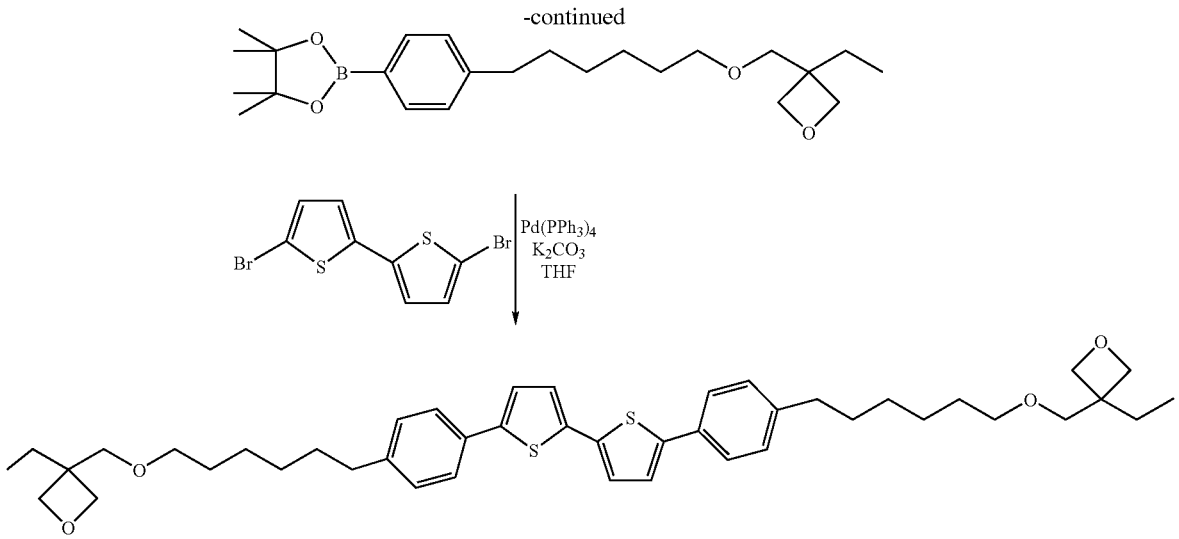

Step 14.1: 3-[6-(4-Bromophenyl)hexyloxymethyl]-3-ethyloxetane

To a mixture of zinc powder (1.80 g, 27.5 mmol) in anhydrous DMA (20 ml) is added iodine (0.5 g, 1.97 mmol). This mixture is stirred until the red color of iodine disappeared (ca. 2 min), followed by the addition of 3-(6-bromohexyloxymethyl)-3-ethyloxetane (5.0 g, 17.9 mmol) and the resultant mixture is stirred at 85° C. for 4.5 h, then cooled to room temperature. In another flask charged with anhydrous THF (30 ml) is added 1-bromo-4-iodobenzene (7.0 g, 24.74 mmol) and Pd(dppf)Cl$_2$ (0.5 g, 0.61 mmol). This mixture is stirred for 10 min, then the organic zinc reagent above is introduced. The reaction mixture is stirred overnight (~16 h) at room temperature. Sat. aq. NH$_4$Cl solution is added and the mixture is extracted with ethyl acetate (3×70 ml). The extracts are dried (Na$_2$SO$_4$) and evaporated under reduced pressure. The residue is purified by column chromatography on silica, eluting with petrol/ethyl acetate (10:0 to 4:1), to give a brown oil (2.6 g, 41%). $^1$H NMR (300 MHz, CDCl$_3$): δ(ppm) 7.35 (d, J=8.4 Hz, 2H, Ar—H), 7.01 (d, J=8.4 Hz, 2H, Ar—H), 4.43 (d, J=5.7 Hz, 2H, OCH$_2$), 4.34 (d, J=5.7 Hz, 2H, OCH$_2$), 3.48 (s, 2H, OCH$_2$), 3.41 (t, J=6.4 Hz, 2H, OCH$_2$), 2.53 (t, J=7.9 Hz, 2H, ArCH$_2$), 1.72 (q, J=7.6 Hz, 2H, CH$_2$), 1.56 (m, 4H, CH$_2$), 1.34 (m, 4H, CH$_2$); 0.86 (t, J=7.6 Hz 3H, CH$_3$); $^{13}$C NMR (75 MHz, CDCl$_3$): δ (ppm) 141.6 (quat.), 131.2 (CH), 130.2 (CH), 119.3 (quat.), 78.4 (OCH$_2$), 73.4 (OCH$_2$), 71.4 (OCH$_2$), 43.4 (quat.), 35.3 (CH$_2$), 31.3 (CH$_2$), 29.5 (CH$_2$), 29.0 (CH$_2$), 26.8 (CH$_2$), 26.0 (CH$_2$), 8.2 (CH$_3$).

Step 14.2: 2-{4-[6-((3-ethyloxetan-3-yl)methoxy)hexyl]phenyl}-4,4,5,5-tetramethyl-[1,3,2]-dioxaborolane To a stirred solution of 3-[6-(4-bromophenyl)hexyloxymethyl]-3-ethyl-oxetane (2.0 g, 5.63 mmol) in dry THF (20 ml) is added n-butyllithium (2.5 M in hexanes, 2.25 ml, 5.63 mmol) dropwise at −78° C. under nitrogen, with stirring. After complete addition, the mixture is stirred for another 20 min, followed by the addition of 2-isopropoxy-4,4,5,5-tetramethyl-1,3,2-dioxaborolane (1.05 g, 5.64 mmol). The resultant mixture is stirred overnight at room temperature. The reaction is quenched with water, and the reaction mixture is extracted with ethyl acetate (3×50 ml). The combined organic extracts are washed with water, brine, and dried (Na$_2$SO$_4$). The solvent is removed under reduced pressure and the residue is purified by column chromatography on silica, eluting with petroleum ether/ethyl acetate (9:1 to 7:3), to give a brown oil (1.60 g, 71%). $^1$H NMR (300 MHz, CDCl$_3$): δ(ppm) 7.72 (d, J=8.1 Hz, 2H, Ar—H), 7.17 (d, J=8.1 Hz, 2H, Ar—H), 4.43 (d, J=5.8 Hz, 2H, OCH$_2$), 4.35 (d, J=5.8 Hz, 2H, OCH$_2$), 3.48 (s, 2H, OCH$_2$), 3.41 (t, J=6.4 Hz, 2H, OCH$_2$), 2.60 (t, J=7.9 Hz, 2H, ArCH$_2$), 1.72 (q, J=7.5 Hz, 2H, CH$_2$), 1.56 (m, 4H, CH$_2$), 1.32 (m, 14H, CH$_2$ and CH$_3$); 0.86 (t, J=7.5 Hz 3H, CH$_3$); $^{13}$C NMR (75 MHz, CDCl$_3$): δ (ppm) 146.1 (quat.), 134.8 (CH), 127.8 (CH), 83.5 (quat.), 78.5 (OCH$_2$), 73.3 (OCH$_2$), 71.5 (OCH$_2$), 43.4 (quat.), 36.1 (CH$_2$), 31.3 (CH$_2$), 29.5 (CH$_2$), 29.0 (CH$_2$), 26.7 (CH$_2$), 26.0 (CH$_2$), 24.8 (CH$_3$), 8.2 (CH$_3$).

Step 14.3

A 20 ml microwave tube is charged with 5,5'-dibromothiophene (0.20 g, 0.62 mmol), tetrakis(triphenylphosphine)palladium(0) (0.05 g, 0.04 mmol), 2-{4-[6-((3-ethyloxetan-3-yl)methoxy)-hexyl]phenyl}4,4,5,5-tetramethyl-1,3,2-dioxaboro-nlane (0.75 g, 1.86 mmol), anhydrous THF (7 ml) and tetrabutylammonium hydroxide (20% in water, 2 ml). The tube is sealed and heated and stirred in a microwave reactor (Emrys Creator) for 1 min at 100° C., 1 min at 120° C. and 15 min at 140° C. After cooling, the mixture is poured into water (100 ml). The precipitate is filtrated off and washed with water and diethyl ether, to give a blue solid, which is purified by column chromatography on silica, eluting with petroleum ether/ethyl acetate (9:1 to 4:1), to give a yellow solid (0.23 g, 52%). $^1$H NMR (300 MHz, CDCl$_3$): δ (ppm) 7.52 (d, J=8.3 Hz 4H, Ar—H), 7.19 (m, 6H, Ar—H), 7.14 (d, J=3.8 Hz, 2H, Ar—H), 4.45 (d, J=5.8 Hz, 4H, OCH$_2$), 4.38 (d, J=5.8 Hz, 4H, OCH$_2$), 3.52 (s, 4H, OCH$_2$), 3.45 (t, J=6.4 Hz, 4H, OCH$_2$), 2.62 (t, J=7.3 Hz 4H, ArCH$_2$), 1.74 (q, J=7.5 Hz, 4H, CH$_2$), 1.60 (m, 8H, CH$_2$), 1.38 (m, 8H, CH$_2$), 0.88 (t, J=7.5 Hz, 6H, CH$_3$); $^{13}$C NMR (75 MHz, CDCl$_3$): δ (ppm) 143.2 (quat.), 142.5 (quat.), 136.3 (quat.), 131.6 (quat.), 129.0 (CH), 125.5 (CH), 124.3 (CH), 123.3 (CH), 78.7 (OCH$_2$), 73.4 (OCH$_2$), 71.6 (OCH$_2$), 43.4 (quat.), 35.6 (CH$_2$), 31.4 (CH$_2$), 29.5 (CH$_2$), 29.1 (CH$_2$), 26.8 (CH$_2$), 26.1 (CH$_2$), 8.3 (CH$_3$).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

The invention claimed is:

1. A compound of formula I

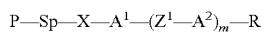

P—Sp—X—A$^1$—(Z$^1$—A$^2$)$_m$—R    I wherein
P is a polymerisable or reactive group,
Sp is a spacer group or a single bond,
X is a linkage group or a single bond,
A$^1$ and A$^2$ are independently of each other 1,4-phenylene or thiophene-2,5-diyl which is optionally substituted with one or more groups R$^1$,
R$^1$ has one of the meanings of R,
Z$^1$ and Z$^2$ are independently of each other —O—, —S—, —CO—, —COO—, —OCO—, —O—COO—, —CO—NR$^0$—, —NR$^0$—CO—, —O—CO—NR$^0$—, —NR$^0$—CO—O—, —NR$^0$—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond,
R$^0$ and R$^{00}$ are independently of each other H or alkyl with 1 to 12 C-atoms,
Y$^1$ and Y$^2$ are independently of each other H, F, Cl or CN,
R is halogen, CN, NO$_2$, NCS, SF$_5$, Sn(R')$_3$, SiR'R''R''', straight chain, branched or cyclic alkyl with 1 to 30 C-atoms, which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR'R''—, —CO—, —COO—, —OCO—, —OCO—O—, —S—CO—, —CO—S—, —CY$^1$=CY$^2$— or —C≡C— in such a manner that O and/or S atoms are not linked directly to one another, an aromatic or heteroaromatic group, or P—Sp—X,
R', R'' and R''' are independently of each other alkyl with 1 to 12 C-atoms, and
m is 3, 4 or 5,
with the provisos that
a) all five or six of A$^1$ and A$^2$ are thiophene-2,5-diyl, or two of A$^1$ and A$^2$ are 1,4-phenylene and two of A$^1$ and A$^2$ are thiophene-2,5-diyl,
wherein all thiophene and phenylene groups are optionally substituted with one or more R$^1$ groups, and
b) A$^1$ and A$^2$ are different from

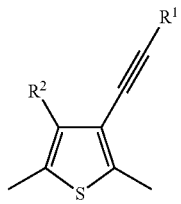

wherein R$^2$ is R$^1$ or —C≡C—R$^1$ and the groups R$^1$ have independently of each other one of the meanings of R given above.

2. A compound according to claim 1, wherein R is is alkyl or alkoxy with 1 to 15 C atoms which is optionally mono-, poly- or perfluorinated.

3. A compound according to claim 1, wherein R is P—Sp—.

4. A compound according to claim 1, wherein X is —O—, —O—CH$_{12}$—, —CH$_2$—O— or a single bond.

5. A compound according to claim 1, wherein all groups Z$^1$, A$^1$, and A$^2$, and optionally X, form a conjugated system.

6. A compound according to claim 1, wherein Z$^1$ is a single bond or a conjugated link, or —CY$^1$=CY$^2$— or —C≡C—.

7. A compound according to claim 1, which is of one of the following formulae

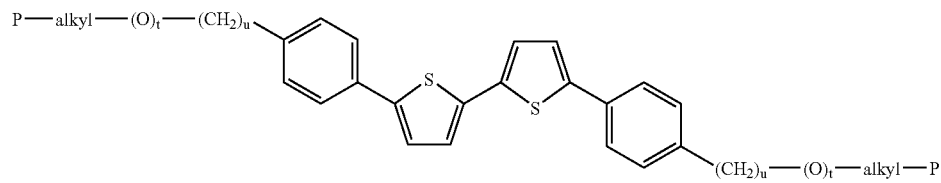

I1a1

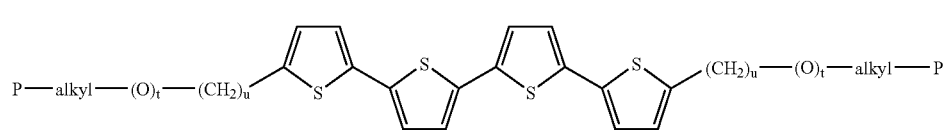

I2a1

-continued

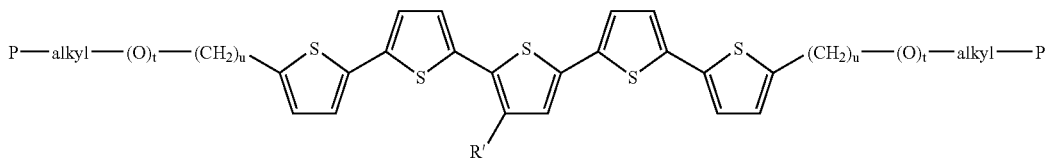

I2c1

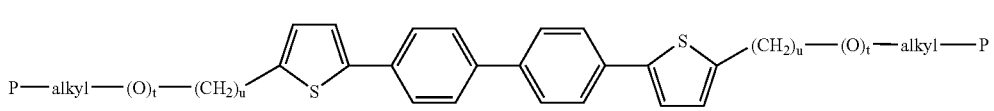

I7a

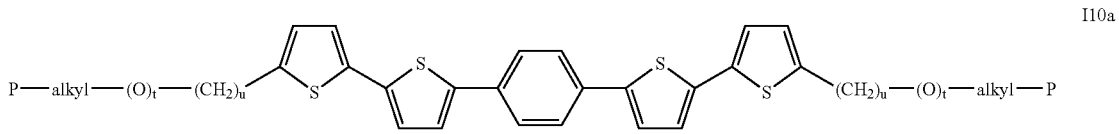

I10a wherein
P¹ and P² are identical or different groups P as defined in claim 1,
Sp¹ and Sp² are identical or different groups Sp as defined in claim 1
X¹ and X² are identical or different groups X as defined in claim 1,
R is as defined in claim 1,
R¹ to R¹² have independently of one another one of the meanings of R¹ in claim 1, and
r is 0, 1, 2, 3 or 4.

8. A compound according to claim 7, which is of one of the following formulae

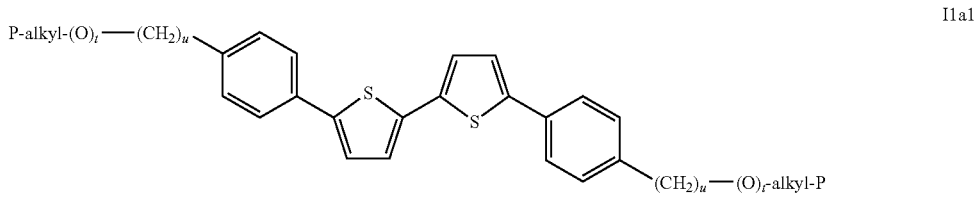

I1a1

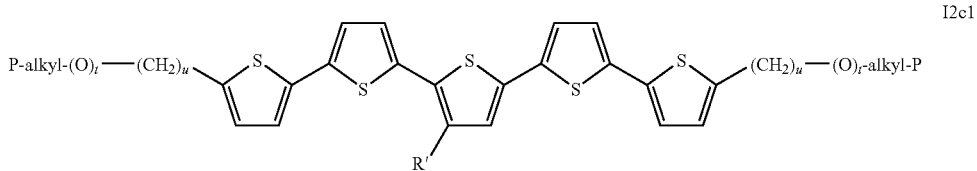

I2c1

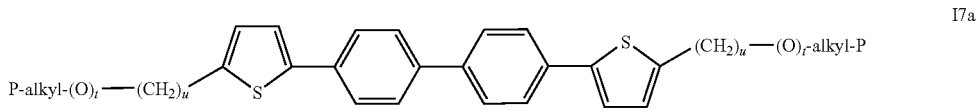

I7a wherein "alkyl" is an alkylene group with 1 to 12 C-atoms,
t is 0 or 1,
u is 0 or 1,
R' is H or optionally fluorinated $C_{1-8}$ alkyl,
P is $CH_2$=CW—COO—,

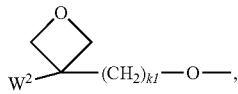

$(CH_2$=CH$)_2$CH—OCO— or $(CH_2$=CH—CH$_2)_2$N—CO—, W is H, $CH_3$, Cl or CN,
$W^2$ is H or alkyl with 1 to 5 C-atoms, and
k1 is 0 or 1.

9. A compound according to claim 1, wherein P, is $CH_2$=$CW^1$—COO—,

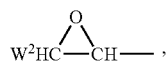

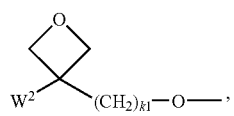

$CH_2$=$CW^2$—$(O)_{k1}$—, $CH_3$—CH=CH—O—, $(CH_2$=CH$)_2$ CH—OCO—, $(CH_2$=CH—CH$_2)_2$CH—OCO—, $(CH_2$=CH$)_2$CH—O—, $(CH_2$=CH—CH$_2)_2$N—, $(CH_2$=CH—CH$_2)_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—$(COO)_{k1}$-Phe-$(O)_{k2}$—, Phe-CH=CH—, HOOC—, OCN—, and $W^4W^5W^6$Si—, with $W^1$ being H, Cl, CN, phenyl or alkyl with 1 to 5 C-atoms, $W^2$ and $W^3$ being independently of each other H or alkyl with 1 to 5 C-atoms, $W^4$, $W^5$ and $W^6$ being independently of each other Cl, oxaalkyl or oxacarbonylalkyl with 1 to 5 C-atoms, Phe being 1,4-phenylene that is optionally substituted by one or more groups as defined in claim 1, and $k_1$, and $k_2$ being independently of each other 0 or 1.

10. A compound according to claim 1, that exhibits a liquid crystal phase.

11. A reactive liquid crystal mixture comprising one or more compounds according to claim 1 and optionally one or more further reactive compounds, wherein at least one of the compounds is mesogenic or liquid crystalline.

12. An anisotropic polymer obtainable from a compound according to claim 1 or from a mixture containing said compound.

13. An anisotropic polymer with charge transport properties obtainable from a compound according to claim 1 or from a mixture containing said compound, which are aligned in their liquid crystal phase into macroscopically uniform orientation and polymerised or crosslinked to fix the oriented state.

14. A side chain liquid crystal polymer obtained by polymerisation of a compound according to claim 1 or from a mixture containing said compound, or by grafting the compound or the mixture components to a polymer backbone in a polymeranalogous reaction, optionally with one or more additional mesogenic or non-mesogenic comonomers.

15. A semiconductor or charge transport material, an optical, electrooptical or electronic device, a component of integrated circuitry, a field effect transistor, a thin film transistor in a flat panel display application, a radio frequency identification tag, a semiconducting component for an organic light emitting diode application, an electroluminescent display or backlight, a liquid crystal display, a photovoltaic or sensor device, an electrode material in a battery, a photoconductor, an electrophotographic application, an electrophotographic recording, a light-modulating component for a liquid crystal display, an optical film or an optical or electrooptical device comprising a compound according to claim 1 or a mixture containing said compound or a polymer obtained from the compound or the mixture.

16. A field effect transistor, a component of integrated circuitry, a thin film transistor in a flat panel display application, or a radio frequency identification tag, comprising a compound according to claim 1 or a mixture containing said compound or a polymer obtained from the compound or the mixture.

17. A security marking or device comprising a compound according to claim 1 or a mixture containing said compound or a polymer obtained from the compound or the mixture.

18. A compound according to claim 1 or a mixture containing said compound or a polymer obtained from the compound or the mixture, which are oxidatively or reductively doped to form conducting ionic species.

19. A charge injection layer, a planarising layer, an antistatic film or conducting substrate or pattern for an electronic application or flat panel display, comprising a compound, mixture or polymer according to claim 18.

20. A compound according to claim 1, wherein $A^1$ and $A^2$ are different from

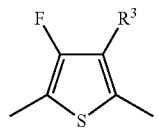 and 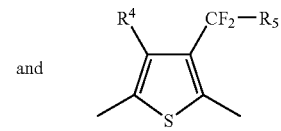

wherein $R^3$ is straight chain, branched or cyclic alkyl with 1 to 20 C-atoms, which is unsubstituted, mono- or poly-substituted by F, Cl, Br, I or CN, and wherein one or more non-adjacent $CH_2$ groups are optionally replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=OH— or —C≡C— in such a manner that O and/or S atoms are not linked directly to one another, or optionally substituted aryl or heteroaryl, $R^4$ is H, F or $R^3$, $R^5$ is H, straight chain, branched or cyclic alkyl with 1 to 20 C-atoms wherein one or more, but not all, H atoms are optionally replaced by F, Cl, Br, I or CN, and wherein one or more non-adjacent $CH_2$ groups are optionally replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=OH— or —C≡C— in such a manner that O and/or S atoms are not linked directly to one another, or optionally substituted aryl or heteroaryl, with $R^0$ and $R^{00}$ being as defined in formula I.

21. A compound according to claim 1, wherein all of $A^1$ and $A^2$ are unsubstituted thiophene or phenylene groups.

22. A semiconductor or charge transport material, an optical, electrooptical or electronic device, a component of integrated circuitry, a field effect transistor, a thin film transistor in a flat panel display application, a radio frequency identification tag, a semiconducting component for an organic light emitting diode application, an electroluminescent display or backlight, a liquid crystal display, a photovoltaic or sensor device, an electrode material in a battery, a photoconductor, an electrophotographic application, an electrophotographic recording, a light-modulating component for a liquid crystal display, an optical film or an optical or electrooptical device comprising a compound according to claim 1.

23. A field effect transistor, a component of integrated circuitry, a thin film transistor in a flat panel display application, or a radio frequency identification tag, comprising a compound according to claim 1.

24. A security marking or device comprising a compound according to claim 1.

25. A charge injection layer, a planarising layer, an antistatic film or conducting substrate or pattern for an electronic application or flat panel display, comprising a compound according to claim 1.

* * * * *